(12) United States Patent
Glavina et al.

(10) Patent No.: US 11,002,747 B2
(45) Date of Patent: May 11, 2021

(54) SYSTEMS AND METHODS FOR ASSURING QUALITY COMPLIANCE OF POINT-OF-CARE INSTRUMENTS USED WITH SINGLE-USE TESTING DEVICES

(71) Applicant: Abbott Point of Care Inc., Princeton, NJ (US)

(72) Inventors: Paul Glavina, Kanata (CA); Jody Ann Tirinato, Plainsboro, NJ (US)

(73) Assignee: Abbott Point of Care Inc., Princeton, NJ (US)

( * ) Notice: Subject to any disclaimer, the term of this patent is extended or adjusted under 35 U.S.C. 154(b) by 165 days.

(21) Appl. No.: 15/145,899

(22) Filed: May 4, 2016

(65) Prior Publication Data
US 2016/0356801 A1  Dec. 8, 2016

Related U.S. Application Data

(60) Provisional application No. 62/171,689, filed on Jun. 5, 2015.

(51) Int. Cl.
*G01N 35/00* (2006.01)
*G16H 40/40* (2018.01)
*G16H 10/40* (2018.01)

(52) U.S. Cl.
CPC ... *G01N 35/00623* (2013.01); *G01N 35/0092* (2013.01); *G01N 35/00693* (2013.01); *G01N 35/00732* (2013.01); *G01N 35/00871* (2013.01); *G16H 10/40* (2018.01); *G16H 40/40* (2018.01);
(Continued)

(58) Field of Classification Search
CPC ........ G16H 10/40; G16H 40/40; H04L 67/12; H04L 67/125; G01N 35/00871; G01N 2035/00881; G01N 35/00623; G01N 2035/00653
See application file for complete search history.

(56) References Cited

U.S. PATENT DOCUMENTS

| | | |
|---|---|---|
| 4,954,087 A | 9/1990 | Lauks et al. |
| 5,096,669 A | 3/1992 | Lauks et al. |
| 5,112,455 A | 5/1992 | Cozzette et al. |

(Continued)

FOREIGN PATENT DOCUMENTS

| | | | | |
|---|---|---|---|---|
| WO | WO-2012037079 A1 * | 3/2012 | ....... | G01N 35/00623 |
| WO | 2012084063 A1 | 6/2012 | | |

OTHER PUBLICATIONS

"i-STAT®1 System Manual," Abbott Point of Care, Nov. 2014, downloaded from the internet at <https://www.massgeneral.org/pathology/assets/poct/i-STAT%20device%20and%20software%20manual%20Nov%202014-LTR21399.pdf> on Dec. 8, 2018. (Year: 2014).*

(Continued)

*Primary Examiner* — Christopher Adam Hixson
*Assistant Examiner* — Michelle Adams
(74) *Attorney, Agent, or Firm* — Kilpatrick Townsend & Stockton LLP

(57) ABSTRACT

The present invention relates to systems and methods of determining quality compliance for one or more biological sample testing instruments used with one or more type of single-use blood testing cartridge, at the point-of-care in a hospital, or other location that deliver medical care. In particular, the systems and methods ensure that only instruments that pass a quality assurance protocol are used for point-of-care testing.

15 Claims, 8 Drawing Sheets

(52) U.S. Cl.
CPC .............. *G01N 2035/00702* (2013.01); *G01N 2035/00752* (2013.01); *G01N 2035/00881* (2013.01)

(56) References Cited

U.S. PATENT DOCUMENTS

| | | | |
|---|---|---|---|
| 5,124,661 | A | 6/1992 | Zelin et al. |
| 5,532,941 | A * | 7/1996 | Lin .................... G16H 10/40 |
| | | | 702/84 |
| 6,512,986 | B1 | 1/2003 | Harmon |
| 6,856,928 | B2 | 2/2005 | Harmon |
| 7,419,821 | B2 | 9/2008 | Davis et al. |
| 7,552,071 | B2 | 6/2009 | Tirinato et al. |
| 7,824,612 | B2 | 11/2010 | Fuisz et al. |
| 7,925,461 | B2 * | 4/2011 | Yamaguchi ........... G16H 40/40 |
| | | | 702/84 |
| 8,495,797 | B2 | 7/2013 | La See |
| 2002/0116224 | A1 | 8/2002 | Hengerer et al. |
| 2002/0133255 | A1 | 9/2002 | Wardlaw et al. |
| 2004/0173456 | A1 | 9/2004 | Boos et al. |
| 2007/0255756 | A1 * | 11/2007 | Satomura .......... G01N 35/00663 |
| 2008/0217407 | A1 * | 9/2008 | Ackermann ........... G16H 40/40 |
| | | | 235/439 |
| 2011/0150705 | A1 | 6/2011 | Doyle et al. |
| 2011/0295091 | A1 | 12/2011 | Azer et al. |
| 2012/0232367 | A1 * | 9/2012 | Allegri .................. A61B 5/145 |
| | | | 600/365 |
| 2013/0002279 | A1 | 1/2013 | Martin et al. |
| 2013/0343955 | A1 | 12/2013 | Doyle et al. |
| 2014/0172315 | A1 | 6/2014 | Vandersleen et al. |

OTHER PUBLICATIONS

International Search Report and Written Opinion dated Jun. 23, 2016, issued in PCT/US2016/030647, 14 pages.
European Application No. EP16723605.8, "Office Action", dated Jan. 30, 2020, 8 pages.

* cited by examiner

SYSTEMS AND METHODS FOR ASSURING QUALITY COMPLIANCE OF POINT-OF-CARE INSTRUMENTS USED WITH SINGLE-USE TESTING DEVICES

CROSS-REFERENCE TO RELATED APPLICATIONS

This application claims priority to U.S. Provisional Application No. 62/171,689, filed on Jun. 5, 2015, the entirety of which is incorporated herein by reference.

FIELD OF THE INVENTION

The technical character of the present invention relates to systems and methods of determining quality compliance for one or more biological sample testing instruments used with one or more type of single-use blood testing cartridge, at the point-of-care in a hospital, or other location that deliver medical care. In particular, the systems and methods implement risk management to ensure that only instruments that pass a quality assurance protocol are used for point-of-care testing.

BACKGROUND OF THE INVENTION

Point-of-care (POC) sample analysis systems are generally based on one or more re-usable test instruments (e.g., a reading apparatus) that perform sample tests using a single-use disposable testing device, e.g., a cartridge or strip that contains analytical elements, e.g., electrodes or optics for sensing analytes such as pH, oxygen and glucose. The disposable testing device can include fluidic elements (e.g., conduits for receiving and delivering the sample to sensing electrodes or optics), calibrant elements (e.g., aqueous fluids for standardizing the electrodes with a known concentration of analyte), and dyes with known extinction coefficients for standardizing optics. The instrument or reading apparatus contains electrical circuitry and other components for operating the electrodes or optics, making measurements, and performing computations. The instrument or reading apparatus also has the ability to display results and communicate those results to laboratory and hospital information systems (LIS and HIS, respectively), for example, via a computer workstation or other data management system. Communication between the instrument or reading apparatus and a workstation, and between the workstation and a LIS or HIS, can be via, for example, an infrared link, a wired connection, wireless communication, or any other form of data communication that is capable of transmitting and receiving electrical information, or any combination thereof. A notable point-of-care system (The i-STAT® System, Abbott Point of Care Inc., Princeton, N.J.) is disclosed in U.S. Pat. No. 5,096,669, which comprises a disposable device, operating in conjunction with a hand-held analyzer, for performing a variety of measurements on blood or other fluids.

One benefit of point-of-care sample testing systems is the elimination of the time-consuming need to send a sample to a central laboratory for testing. Point-of-care sample testing systems allow a nurse or doctor (user or operator), at the bedside of a patient, to obtain a reliable quantitative analytical result, comparable in quality to that which would be obtained in a laboratory. In operation, the nurse selects testing device with the required panel of tests, draws a biological sample from the patient, dispenses it into the testing device, optionally seals the testing device, and inserts the testing device into the instrument or reading apparatus. While the particular order in which the steps occur may vary between different point-of-care systems and providers, the intent of providing rapid sample test results close to the location of the patient remains. The instrument or reading apparatus then performs a test cycle, i.e., all the other analytical steps required to perform the tests. Such simplicity gives the doctor quicker insight into a patient's physiological status and, by reducing the time for diagnosis or monitoring, enables a quicker decision by the doctor on the appropriate treatment, thus enhancing the likelihood of a successful patient outcome.

In the emergency room and other acute-care locations within a hospital, the types of sample tests required for individual patients tend to vary. Thus, point-of-care systems generally offer a range of disposable testing devices with different sample tests, or combinations of tests. For example, for blood analysis devices, in addition to traditional blood tests, the different sample tests may include oxygen, carbon dioxide, pH, potassium, sodium, chloride, hematocrit, glucose, urea, creatinine and calcium, other tests can include, for example, prothrombin time (PT), activated clotting time (ACT), activated partial thromboplastin time (APTT), cardiac troponin I (cTnI), brain natriuretic peptide (BNP), creatine kinase MB (CKMB) and lactate. While devices typically contain between one and ten tests, it should be appreciated by persons of ordinary skill in the art that any number of tests may be contained on a device. For example, a device for genetic screening may include numerous tests. To illustrate the need for different devices, a patient suspected of arrhythmia may require a device with a test combination that includes a potassium test, whereas a patient suspected of a diabetic hypoglycemia may require a device with a test combination that includes a glucose test. An emergency room will need to have sufficient inventory of both types of testing device to meet the anticipated workload.

For hospitals, the introduction of point-of-care testing capabilities has created unique requirements and issues for quality compliance, system and operator verification, and process management. These issues arise from the use of one or more test instruments running multiple types of disposable sample testing devices at various locations within a hospital. Consequently, a hospital must provide an adequate supply of each type of device at each site of use, while ensuring the devices are within their usable shelf-life, along with also ensuring that the instruments are performing to specification. The Clinical Laboratory Improvement Amendments (CLIA) regulate laboratory testing and require clinical laboratories implementing point-of-care sample analysis systems to be certificated by their state as well as the Center for Medicare and Medicaid Services (CMS) before they can accept human samples for diagnostic testing. CLIA has established minimum standards for all non-waived laboratory testing, including specific regulations for quality control.

To achieve the goal of quality control, including the precision and accuracy of test results, it is necessary to be able to detect errors within the point-of-care systems as soon as possible. Conventionally, many point-of-care testing devices include unit-use cartridges and test strips (e.g., single-use disposable testing devices). With unit-use formats, analysis of liquid quality control can verify the performance of an individual test, but the analysis of liquid quality control consumes the test strip or cartridge and cannot guarantee the quality of tests from other strips or cartridges. Thus, unit-use tests often contain internal control processes built into each test to ensure result quality on each strip or cartridge. For example, U.S. Pat. No. 6,512,986 discloses a method of processing test results to detect any random and systemic exception from historical test results that have previously been stored. Further, U.S. Patent Application Publication No. 2002/0116224 discloses a networked expert system for automated evaluation and quality control of point-of-care laboratory measuring data.

However, with many point-of-care testing systems, issues arise in striking a balance between the use of liquid quality control and the reliance on internal control processes built into each test. For example, should an operator of a point-of-care testing device have to use liquid control for each reaction occurring on a sensing chip each day of testing, this could be cost prohibitive and duplicative of internal control processes built into the point-of-care testing system. With so many different point-of-care testing devices and control processes available, laboratories need a systematic approach to ensure quality and strike the right balance of liquid quality control in concert with internal control processes. This approach is known as risk management.

The Clinical and Laboratory Standards Institute (CLSI) guideline EP-23 introduces risk management principles to the clinical laboratory. CLIS EP23 describes good laboratory practice for developing a quality control plan based on the manufacturer's risk information, applicable regulatory and accreditation requirements, and the individual healthcare and laboratory setting. This guideline helps laboratories identify weaknesses in the testing process that could lead to error and explains how to develop a plan to detect and prevent those errors from happening. The CMS has incorporated key elements of risk management from CLSI EP23 into the new CLIA interpretive guidelines that offer a quality control option called an Individualized Quality Control Plan (IQCP). Specifically, laboratory tests, including point-of-care testing, now have two options for defining the frequency of quality control for non-waved testing (e.g., moderate- and high-complexity tests) including either two concentrations of liquid quality control each day, or developing an IQCP.

IQCPs are valuable to laboratories or medical care facilities that use single unit-use point-of-care devices and instrumentation with built-in control processes. The primary objective of IQCPs is not to reduce the frequency of analyzing liquid quality control, but rather to ensure the right quality control to address a laboratory's or medical care facility's specific risks and ensure quality test results. In the context of point-of care testing, laboratories or medical care facilities may incorporate both internal and external control processes. Each device is unique, operates differently, and offers specific control processes engineered into the test. And since no single control process can cover all potential risks, a laboratory's or medical care facility's quality control plan should incorporate a mix of internal controls and traditional liquid quality control.

Each test may require a specific IQCP, because devices are different and present unique risks. However, a single risk assessment and IQCP could cover multiple tests conducted on the same instrument, provided the IQCP factors in the differences unique to each analyte. For instance, a single IQCP for a chemistry analyzer could cover all tests conducted on that analyzer, since instrument operation, risk of error, and functionality of control processes is shared amongst all analytes on the same analyzer. IQCPs should benefit medical care facilities in a number of ways. For example, laboratories or medical care facilities using single unit-use devices may define an optimum frequency of liquid quality control in conjunction with a manufacturer's control processes. For unit-use blood gas and coagulation devices, medical care facilities can be more efficient by analyzing quality control for lots of reagents using a subset of devices rather than every device available, since the chemistry of the test is in the unit-use strip or cartridge—not in the device, which acts as a volt-meter or timer. For molecular arrays and labs-on-a-chip, analyzing liquid quality control across each reaction may be less effective than controlling the processes of greatest risk, such as quality and amount of sample, viability of replicating enzyme, and temperature cycling.

Quality control programs, especially point-of-care quality control programs, which monitor numerous instruments and types of devices interconnected within a network, tend to yield large volumes of quality control information obtained from numerous point-of-care locations within the network. Accordingly, several computer implemented methods have been proposed to process the large volumes of quality control information. These computer implemented methods often include processes for determining potential quality control compliance issues. However, the performance of risk management to ensure quality and strike the right balance of liquid quality control in concert with internal control processes has not been adequately addressed. Nor has there been a quality control program implemented using a centrally managed system that ensures only biological sample testing devices that pass a quality assurance protocol are used for point-of-care testing.

For example, U.S. Pat. Nos. 6,856,928 and 6,512,986 disclose a method for analyzing data from point-of-care testing to identify when the testing exceeds a variation expected under stable operation (i.e., the testing is "out of control"). The method includes storing test results received from each of a plurality of point-of-care devices, including an association with the operator of the point-of-care device and/or a reagent used in obtaining the test results. The method further includes processing the results to detect any random and/or systemic exception from results that have previously been stored, and automatically disabling a questionable point-of-care device based on detection of a quality control compliance exception This method, however, is predicated on quality control rules, such as Westgard Rules, for automatically disabling a particular point-of-care device based on detection of an exception, and does not strike a balance of the liquid quality control in concert with internal control processes nor ensure only biological sample testing devices that pass a quality assurance protocol are used for point-of-care testing.

U.S. Pat. No. 8,495,707 discloses system for quality assured analytical testing. The system includes an Instrument Management System and an analytical instrument for conducting analytical testing, the analytical instrument having an input section for determining an actual user of the instrument and the analytical instrument being configured to run a testing routine. The system further includes a terminal connected to the Instrument Management System, which is remote from the analytical instrument and which provides an examination module of the Instrument Management System that is programmed to conduct an exam during which the examination module prompts questions to the user via the terminal which relate to the analytical instrument and/or a diagnostic test to be conducted therewith, receive and evaluate answers to the exam, and transmit a user certificate to the analytical instrument if the user passed the exam such that a user may access a testing routine. This method, however, is predicated on control of instrument usage so that only well-educated users with proven knowledge are allowed to perform testing with the analytical instrument, and does not strike a balance of liquid quality control in concert with the knowledge testing nor ensure only biological sample testing devices that pass a quality assurance protocol are used for point-of-care testing.

U.S. Patent Application Publication No. 2004/0173456 discloses a system for point-of-care diagnosis including a cartridge for analysis, where cartridge-specific data are evaluated for the respective concentration values in accordance to the cartridge specific data and information. Additionally, U.S. Pat. No. 7,824,612 discloses a body fluid analyzer with a data storage unit that contains information concerning a particular drug being taken by a patient, and a processor for setting a threshold value for an analyte to be sensed by a sensing unit and a display for displaying an alert. As with other disclosed methods of point-of-care quality control programs, these methods do not strike a balance of liquid quality control in concert with internal control processes nor ensure only biological sample testing devices that pass a quality assurance protocol are used for point-of-care testing.

In view of the above-noted limitations of conventional point-of-care testing systems and the recent implementation of IQCPs by many laboratories and medical care facilities, there remains a need for systems and methods of determining quality compliance for a set of biological sample testing devices, e.g., single-use blood testing cartridges, used with one or more test instruments at the point-of-care in a hospital or other location for delivering medical care, where the systems and methods implement risk management to ensure that only devices that pass a quality assurance are used for point-of-care testing.

SUMMARY OF THE INVENTION

In one embodiment, the present invention is directed to a method implemented in a computer infrastructure having computer executable code tangibly embodied on one or more non-transitory storage devices having programming instructions. The programming instructions are operable to transmit a requirement for instrument calibration verification from a data manager to one or more instruments based on a predetermined schedule, and in response to the request for the instrument calibration verification, perform the instrument calibration verification using: (i) a predetermined number and type of calibration fluids, a predetermined number of sample testing cartridges of a set of sample testing cartridges, and the one or more instruments, or (ii) an electronic simulator, to generate calibration verification data. The programming instructions are further operable to transmit the calibration verification data from the one or more instruments to the data manager, determine a compliance status of the one or more instruments at the data manager based on whether the calibration verification data is within range of predetermined calibration target values, store the determined compliance status for the one or more instruments in a data table, and transmit the data table from the data manager to each of the one or more instruments. The programming instructions are further operable to enable use of the one or more instruments for performing one or more analytical tests on biological samples when the compliance status stored in the data table indicates the one or more instruments are in compliance, and at least partially disable use of the one or more instruments for performing the one or more analytical tests on the biological samples when the compliance status stored in the data table indicates the one or more instruments are not in compliance.

In some embodiments, the programming instructions are further operable to receive attributes at each of the one or more instruments from the data manager. The attributes including the predetermined number and type of calibration fluids and the predetermined number of testing cartridges of the set of sample testing cartridges. Optionally, the programming instructions are further operable to receive an instrument configuration profile at the data manager from a configuration manager. The configuration profile including the predetermined calibration target values.

In other embodiments, the one or more analytical tests are configured to detect one or more analytes selected from the group consisting of: sodium, potassium, chloride, total carbon dioxide, ionized calcium, glucose, blood urea nitrogen (BUN), creatinine, lactate, hematocrit, pH, partial pressure of carbon dioxide, partial pressure of oxygen, troponin I, troponin T, creatine kinase MB, procalcitonin, beta human chorionic gonadotropin (bHCG), human chorionic gonadotropin (HCG), N-terminal of the prohormone brain natriuretic peptide (NTproBNP), prohormone brain natriuretic peptide (proBNP), brain natriuretic peptide (BNP), myoglobin, parathyroid hormone, d-dimer, neutrophil gelatinase-associated lipocalin (NGAL), galectin-3, and prostate specific antigen (PSA).

In additional or alternative embodiments, the programming instructions are further operable to generate the predetermined schedule comprising a scheduled time for the instrument calibration verification for each of the one or more instruments. The requirement for the instrument calibration verification is transmitted in accordance with the predetermined schedule.

In one embodiment, the present invention is directed to a system comprising a set of sample testing cartridges, and a plurality of analyzers in communication with one another via a wireless network. Each of the plurality of analyzers is configured to perform analyzer calibration verification in response to receiving a requirement for the analyzer calibration verification from a data manager based on a predetermined schedule, wherein the analyzer calibration verification is performed using: (i) a predetermined number and type of calibration fluids and a predetermined number of sample testing cartridges of the set of sample testing cartridges, or (ii) an electronic simulator, to generate calibration verification data. Each of the plurality of analyzers is also configured to transmit the calibration verification data. The system further comprises a data manager that is in communication with each of the plurality of analyzers via the wireless network. The data manager is configured to determine a compliance status of each of the plurality of analyzers based on whether the calibration verification data is within range of predetermined calibration target values, store the determined compliance status for each of the plurality of analyzers in a data table, and transmit the data table to each of the plurality of analyzers. Each of the plurality of analyzers is further configured to when the compliance status stored in the data table indicates an analyzer is in compliance, enable use of the analyzer for performing one or more analytical tests on biological samples, and when the compliance status stored in the data table indicates the analyzer is not in compliance, at least partially disable use of the analyzer for performing the one or more analytical tests on the biological samples.

In some embodiments, the system further comprises a configuration manager configured to obtain the predetermined calibration target values, and transmit an analyzer configuration profile including the predetermined calibration target values to the data manger. Optionally, the data manager is further configured to transmit attributes to each of the plurality of analyzers, the attributes including the predetermined number and type of calibration fluids and the predetermined number of testing cartridges of the set of sample testing cartridges.

In other embodiments, the data manager is further configured to generate the predetermined schedule comprising a scheduled time for the analyzer calibration verification for each of the plurality of analyzers, transmit the requirement for the analyzer calibration verification in accordance with the predetermined schedule, and reset the scheduled time for the analyzer calibration verification for each of the plurality of analyzers when the determined compliance status indicates each of the plurality of analyzers are in compliance.

In one embodiment, the present invention is directed to a computer implemented method comprising in response to a request for the instrument calibration verification, performing one or more quality control tests to generate calibration verification data, the one or more quality control tests being performed using: (i) a predetermined number and type of calibration fluids, (ii) a predetermined number of sample testing cartridges of a set of sample testing cartridges, and (iii) at least one analyzer of a plurality of analyzers. The method further comprising transmitting the calibration verification data to a data manager, and receiving a data table from the data manager. The data table comprising a compliance status for the at least one analyzer that is determined based on the calibration verification data The method further comprising enabling use of the at least one analyzer for performing one or more analytical tests on biological samples when the compliance status stored in the data table indicates the at least one analyzer is in compliance, and at least partially disabling use of the at least one analyzer for performing the one or more analytical tests on the biological samples when the compliance status stored in the data table indicates the at least one analyzer is not in compliance.

In another embodiment, the present invention is directed to a computer implemented method comprising in response to a request for the instrument calibration verification, performing one or more quality control tests to generate calibration verification data, the one or more quality control tests being performed using an electronic simulator, and transmitting the calibration verification data to a data manager. The method further comprises receiving a data table from the data manager, the data table comprising a compliance status for the at least one analyzer that is determined based on the calibration verification data, enabling use of the at least one analyzer for performing one or more analytical tests on biological samples when the compliance status stored in the data table indicates the at least one analyzer is in compliance, and disabling use of the at least one analyzer for performing the one or more analytical tests on the biological samples when the compliance status stored in the data table indicates the at least one analyzer is not in compliance.

In one embodiment, the present invention is directed to a portable clinical analyzer for in vitro analysis. The analyzer comprises a port configured to receive a sample testing cartridge of a set of sample testing cartridges. The analyzer further comprises a computing device configured to in response to a request for the instrument calibration verification, performing one or more quality control tests to generate calibration verification data, the one or more quality control tests being performed using: (i) a predetermined number and type of calibration fluids and a predetermined number of sample testing cartridges of the set of sample testing cartridges, or (ii) an electronic simulator. The computing device is further configured to transmit the calibration verification data to a data manager, and receive a data table from the data manager, the data table comprising a compliance status for the portable clinical analyzer that is determined based on the calibration verification data. The computing device is further configured to enable use of the portable clinical analyzer for performing one or more analytical tests on biological samples when the compliance status stored in the data table indicates the portable clinical analyzer is in compliance, and at least partially disable use of the portable clinical analyzer for performing the one or more analytical tests on the biological samples when the compliance status stored in the data table indicates the portable clinical analyzer is not in compliance.

BRIEF DESCRIPTION OF THE DRAWINGS

The present invention will be better understood in view of the following non-limiting figures, in which.

DETAILED DESCRIPTION OF THE INVENTION

Introduction

Figure 1:
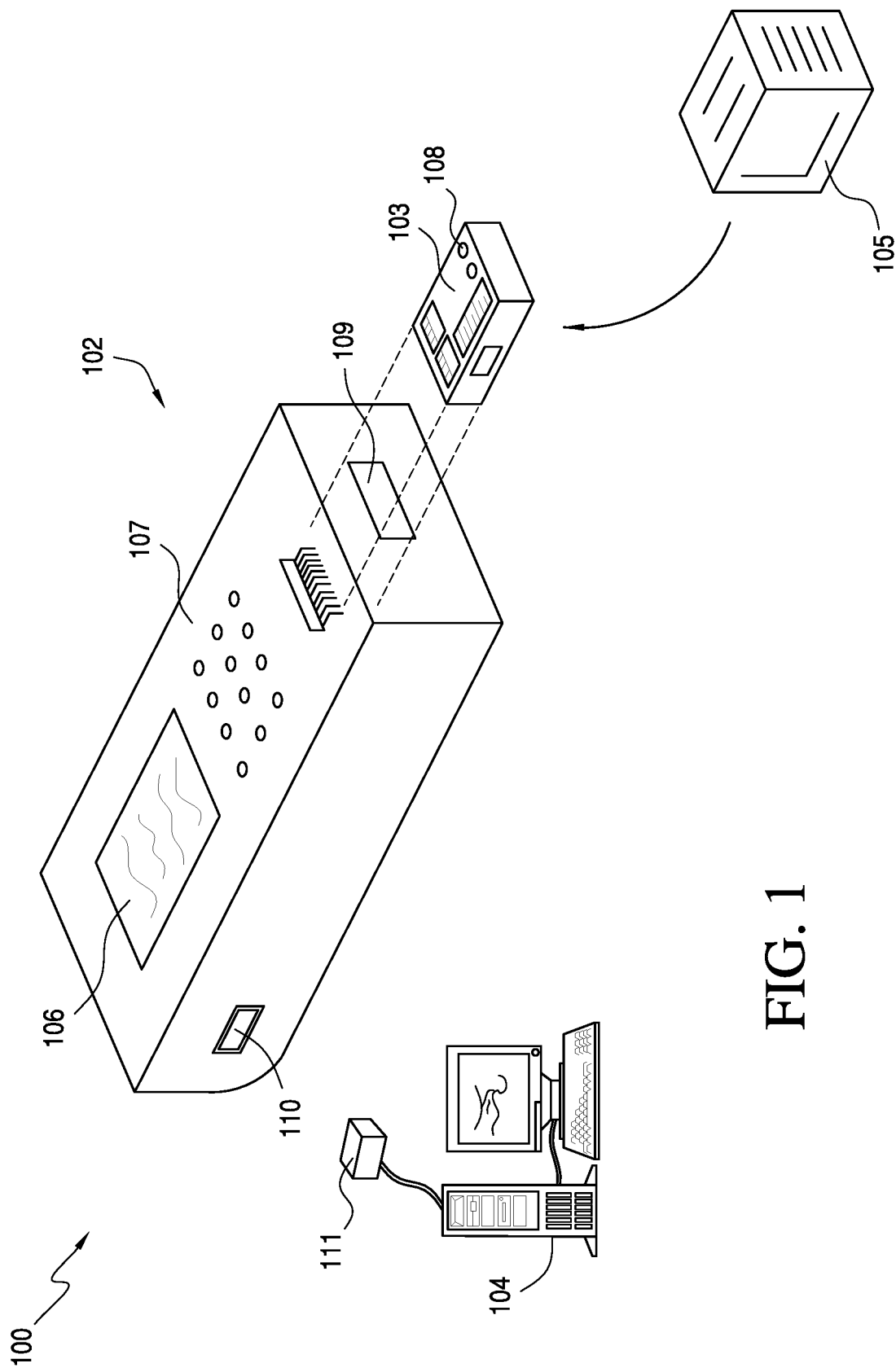
FIG. 1 shows an isometric view of a disposable sensing device and reader device in accordance with some aspects of the invention.

A typical point-of-care testing program in an institution may have tens or hundreds of non-laboratory operators with wide ranges of education, training, responsibilities, and understanding of medical conditions and the indications and implications of medical testing. A challenge of any program for quality control compliance for technologies used for point-of-care blood testing is to assure the technology is compatible with the operator skill levels of those who use the technology. Typically, this is a responsibility of a quality compliance manager in partnership with nursing and other clinical personnel, who construct a quality control system for a medical care facility. To be effective, the technology should be practical and simple to understand. Accordingly, some aspects of the present invention are directed to providing a configuration manager configured to help quality compliance managers to efficiently and effectively construct, implement, and maintain meaningful quality control systems and processes.

More specifically, some embodiments of the present invention are directed to utilizing a configuration manager to develop and implement a program for quality control compliance of technologies that utilize point-of-care sample testing. The program for quality control compliance includes a plurality of attributes that are configurable to ensure that a right amount and type of quality control is implemented to address a laboratory's or medical care facility's specific risks and ensure quality test results. For example, the plurality of attributes may be configured to include procedures for assessing risk and quality as instructed by the CLSI EP23. The plurality of attributes may also be configured to include procedures for the review of incoming quality control test results, intermediate quality control test results, proficiency testing results, and preventive maintenance records (e.g., this may include recording all of the test results obtained by an operator and monitoring the results for inaccuracies).

While performing a quality control test function on a single instrument with a single test device using one or more quality control liquids or fluids is standard practice in the art of blood testing, there is currently no global solution to the issue of managing multiple instruments at distributed locations (and test device types) in a simple, convenient and cost-effective manner. The technical solution of the present invention overcomes this problem using a centrally managed data manager that is networked with each instrument. More specifically, in the present invention, quality control of a network of instruments is coordinated and managed by a centrally managed data manager in accordance with the procedures defined by a configuration manager. This technology has utility for incoming quality control when cartridges are delivered from a manufacture or supplier to a customer, and for intermittent or daily quality control during the time the cartridges are at a customer site before they exceed an expiration date. The advantage of the aforementioned technical solution is of great benefit to a laboratory or medical care facility, such as a hospital, as the centrally managed data manager can use the quality control data from one instrument quality control procedure to update a compliance status for specific devices or cartridges on all the instruments that are networked together, e.g., all the analytical instruments of one type in a hospital. Moreover, the centrally managed data manager can globally control the quality control procedures for each of the instruments within the network.

A central data management system that comprises the aforementioned configuration manager is configured to automatically keep track of the plurality of attributes, compliance thresholds or target values (e.g., a means for evaluating compliance or non-compliance with operation of the instruments), and quality control records associated with each instrument and/or testing device within the program for quality control compliance. In some embodiments, the central data management system may also keep track of records for each operator within the testing program using an operator tracking record and/or profile system. The quality control records may include instrument identifiers (e.g., a serial number for the instrument), analytical test results, clinical control results, proficiency test results, operator identifiers, etc. The proficiency tests or proficiency test results may pertain to testing of previously analyzed specimens with known concentrations of analyte, internal blind testing samples, or external proficiency testing samples configured for statistical quality assurance programs that enable laboratories to assess their performance in conducting test methods.

The advantage of the aforementioned technical solution for centrally managing and implementing a program for quality control compliance is that it will eliminate the technical problems of having to perform a default frequency of two levels of quality control each day on each unit-use test device with liquid quality control and an inability to balance the default frequency of two levels of quality control with unit-use test devices that include internal control systems and processes built into each unit-use test device. For example, implementations of the present invention provide a technical contribution over conventional quality control systems and methods because the technical features of the present invention interoperate to enable or disable use of a set or lot of testing devices by some (e.g., a subset) or all of the instruments in a network based on a plurality of attributes using a centralized computing environment to ensure quality across the network of instruments and strike the right balance of liquid quality control in concert with internal control processes.

Biological Sample Test System

The present invention relates to a handheld In-Vitro Diagnostic (IVD) instrument system including a self-contained disposable sensing device or cartridge (device(s)) and a reader or analyzer (instrument(s)) configured for use at a patient bedside. A fluid sample to be measured is drawn into a sample entry orifice or port in the cartridge and the cartridge is inserted into the analyzer through a slotted opening or port. Measurements performed by the analyzer are output to a display or other output device, such as a printer or data management system via a port on the analyzer to a computer port. Transmission can be via Wi-Fi, Bluetooth link, infrared and the like. For example, the handheld IVD instrument system may be of similar design to the systems disclosed in U.S. Pat. Nos. 5,096,669 and 7,419,821, both of which are incorporated herein by reference in their entireties.

More specifically, a system and method are disclosed for operating a plurality of point-of-care diagnostic test devices (e.g., cartridges). Each device may be configured to perform at least one biological sample analysis, e.g., blood, plasma, urine tests and the like, and each device may have a usable lifetime denoted for example by an expiration date. FIG. 1 shows the component parts and interactions of a typical point-of-care system. The system 100 may include a reading apparatus 102, a disposable device 103, a central data station or data manager 104 and a box of devices 105. The reading apparatus 102 may include, for example, a display 106, electronic memory and a keypad 107 for manual data entry. The disposable device 103 may include, for example, a port 108 for receiving a patient sample, and the device 103 may be inserted into the reading apparatus 102 through a slotted opening 109. The reading apparatus 102 may communicate with the central data manager 104 using, for example, a wireless connection, an infrared link, an optical link, a network connection 110, 111, or any other form of communication link that uses any form of communication protocol to transfer information.

The reading apparatus 102 may include a barcode reader for reading information from a patient's bar-coded wristband, from a barcode on a device 103 or from any other item (e.g., the box of devices 105, box of control fluids, etc.) used in conjunction with the reading apparatus 102. Other such encoding arrangements can be used. For example, the reading apparatus 102 may also include (either alternatively or in addition to the barcode reader) a radio-frequency (RF) identification device that is capable of identifying an RF tag that is contained on or in each individual device or each box of devices 105. According to another exemplary embodiment of the present invention, one or more of the encoding arrangements may be based upon a binary coding pin array of the type disclosed in, for example, U.S. Pat. No. 4,954,087, which is incorporated herein by reference in its entirety.

The various encoding arrangements may convey relevant information such as, for example, the identity of a specific device type, date and location of manufacture, manufacturing lot number, expiration date, a unique number associated with a device, coefficients for use by the reading apparatus 102 associated with the calculation of blood or other sample parameters, and the like. The device 103 may be used for measurements selected from groups such as, for example, amperometric, potentiometric, conductimetric, optical, and the like. Other relevant information of this general type is well known in the medical manufacturing art, as is the technology for bar coding and barcode recognition.

Other information encoded with the device 103 may include the refrigerator shelf life, the ambient temperature shelf life, the age of the device and the like. Alternatively, rather than including numerous elements of relevant information, a single piece of information, e.g., a lot number, may be included. The lot number may be any alphanumeric sequence or unique identifier that can be used to identify the device 103 and associate relevant information with that device, e.g. quality control attributes. For example, the lot number can be applied to a lookup table or any other type of computer database located within or connected to the reading apparatus 102 or any other computing system, e.g., the data manager 104. Using the lookup table or computer database, relevant shelf life or other such information can be associated with the lot number such that, based on the lot number, the refrigerator shelf life, the ambient temperature shelf life, the age of the device 103 and the like can be determined. Other quality control data or attributes may also be included.

The devices 103 may have a finite refrigerator and ambient temperature shelf life. For example, the devices 103 may have a refrigerated usable lifetime in the range of, for example, about three months to three years, although the devices 103 could have any range of refrigerated usable lifetime. The devices 103 may have an ambient temperature usable lifetime in the range of, for example, about three days to three months, although the devices 103 can have any range of ambient temperature usable lifetime. Given that the devices 103 may have a finite refrigerator and ambient temperature shelf life, there may be a need to ensure that expired devices 103 (e.g., the devices 103 that have exceeded the refrigerated or ambient temperature shelf life) are not used.

Referring to the disposable device 103 and the patient sample entry port 108, the device 103 may perform analyses on a range of biological sample types. These sample types may include, for example, blood, plasma, serum, sputum, cerebrospinal fluid, tears, urine, body tissue, fecal matter, and the like. Appropriate consumable items for use in conjunction with the device 103 are well known in the art. These include, for example, vacutainers, needles, capillary tubes and collection devices, control fluids of different types, syringes, swabs, printer paper, batteries and any other consumable item that can be used in conjunction with the device 103. The consumable items can also be used to facilitate introduction of the sample into the sample entry port 108.

The reading apparatus 102 may include a microprocessor (e.g., any type of processor). The reading apparatus may also include any type of computer memory or any other type of electronic storage medium that is located either internally or externally to the reading apparatus 102, such as, for example, a random access memory (RAM). According to exemplary embodiments, the RAM may contain, for example, the operating program for the reading apparatus 102. As will be appreciated based on the following description, the RAM can, for example, be programmed using conventional techniques known to those having ordinary skill in the art of computer programming. The actual source code or object code for carrying out the steps of, for example, a computer program can be stored in the RAM.

The reading apparatus 102 may include a communications port 110 (e.g., any type of communications port through which electronic information can be communicated over a communications connection, whether locally or remotely) with which the reading apparatus 102 can communicate with, for example, the data manager 104. The reading apparatus 102 may also include the input port 109 that, for example, allows insertion of the device 103 and is appropriately configured to receive the device 103. The reading apparatus 102 may also include a user interface 106, 107. The user interface 106, 107 may be any type of computer monitor or display device on which graphical and/or textual information can be displayed to a user (e.g., through a graphical user interface) and which allows a user to enter information (e.g., commands and the like) through, for example, a keyboard, a touch-screen, any type of pointing device, electronic pen, and the like. For example, the user interface 106, 107 can be configured to receive instructions from the operator of the reading apparatus 102. It should also be appreciated that, while a single reading apparatus 102 is described above; multiple reading apparatus 102 can be included within a system where each is connected to the data manager 104. Typically, each department within a hospital may have one or more readers.

It should further be appreciated by persons of ordinary skill in the art that the devices 103, may in fact be a plurality with each type capable of being used for a different test. The devices 103 can include, for example, blood analysis devices, urine analysis devices, serum analysis devices, plasma analysis devices, saliva analysis devices, cheek swab analysis devices, or any other type of disposable diagnostic device that can be used for point-of-care sample testing.

The data manager 104 may be configured to provide connectivity between individual reading apparatus 102 and central locations, such as, for example, a LIS or HIS (laboratory or hospital information system), and device 103. The data manager 104 may be connected with the various system constituents using any type of communications connection that is capable of transmitting and receiving electronic information, such as, for example, an Ethernet connection or other computer network connection. The data manager 104 can also optionally provide a direct link back to a vendor's (product manufacturer) information system, for example via the Internet, a dial-up connection or other direct or indirect communication link, or through the LIS or HIS. Such an exemplary embodiment can provide for automated re-ordering of devices 103 to maintain the predetermined levels of inventory at a hospital and allow the vendor to forecast demand and adequately plan the manufacture of the devices 103. It can also provide a means for updating device information, e.g. cartridge attributes and profiles, and control fluid information, e.g. expected analyte test ranges.

Exemplary Device or Cartridge

Figure 2:
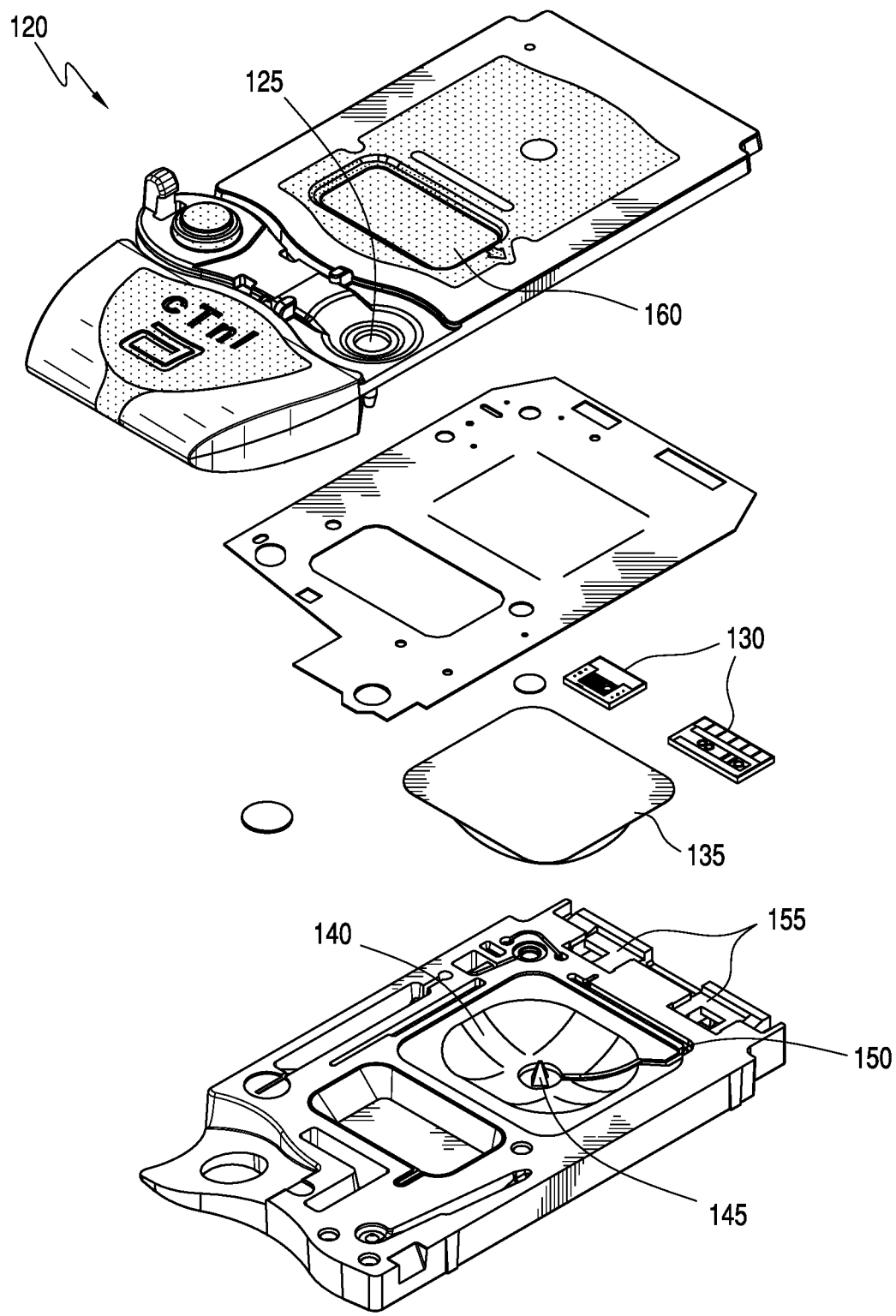
FIG. 2 shows an exploded view of a cartridge in accordance with some aspects of the invention.

FIG. 2 shows an exploded view of cartridge 120 as described in U.S. Patent Application Publication No. 2011/0150705 and U.S. Patent Application Publication No. 2013/0343955, both of which are incorporated herein in their entireties. The cartridge 120 comprises a sample entry port 125, at least one sensor 130 (e.g., an electrochemical sensor, an immunosensor, a hematocrit sensor, a conductivity sensor, etc.), and a pouch 135 containing a fluid, e.g., a sensor-standardization, calibration fluid, and/or wash fluid. The at least one sensor 130 may be substantially aligned to a plane parallel to a horizontal plane of the base of the analyzer. A recessed region 140 of the cartridge 120 preferably includes a spike 145 configured to rupture the pouch 135, upon application of a force upon the pouch 135, for example, by the analyzer 102 (shown in FIG. 1). Once the pouch 135 is ruptured, the system is configured to deliver the fluid contents from the pouch 135 into a conduit 150. Movement of the fluid into and through the conduit 150 and to a sensor region 155 (e.g., a conduit comprising the at least one sensor 130 and a sensing reagent for the sensor) may be effected by a pump, e.g., a pneumatic pump connected to the conduit 150. Preferably, the pneumatic pump comprises a displaceable membrane 160. In the embodiment shown in FIG. 2, the cartridge 120 or test device may be configured to pump fluid via the displaceable membrane 160 from the ruptured pouch 135 and the sample entry port 125 through the conduit 150 and over the sensor region 155. The at least one sensor 130 generates electric signals based on a concentration of specific chemical species in the sample, e.g., performs an electrolyte, metabolite, blood gas or immunoassay on a blood sample from a patient.

The analytes/properties to which the at least one sensor responds generally may be selected from among sodium, potassium, chloride, total carbon dioxide, ionized calcium, glucose, blood urea nitrogen (BUN), creatinine, lactate, hematocrit, pH, partial pressure of carbon dioxide, partial pressure of oxygen, troponin I, troponin T, creatine kinase MB, procalcitonin, beta human chorionic gonadotropin (bHCG), human chorionic gonadotropin (HCG), N-terminal of the prohormone brain natriuretic peptide (NTproBNP), prohormone brain natriuretic peptide (proBNP), brain natriuretic peptide (BNP), myoglobin, parathyroid hormone, d-dimer, neutrophil gelatinase-associated lipocalin (NGAL), galectin-3, and prostate specific antigen (PSA). Preferably, the analyte is tested in a liquid sample that is whole blood, however other samples can be used including blood, plasma, serum, sputum, cerebrospinal fluid, tears, urine, body tissue, and fecal matter and amended forms thereof. Amendments can include diluents and reagents such as anticoagulants and the like.

System Environment

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon, e.g. residing on a data manager.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, RAM, a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 3:
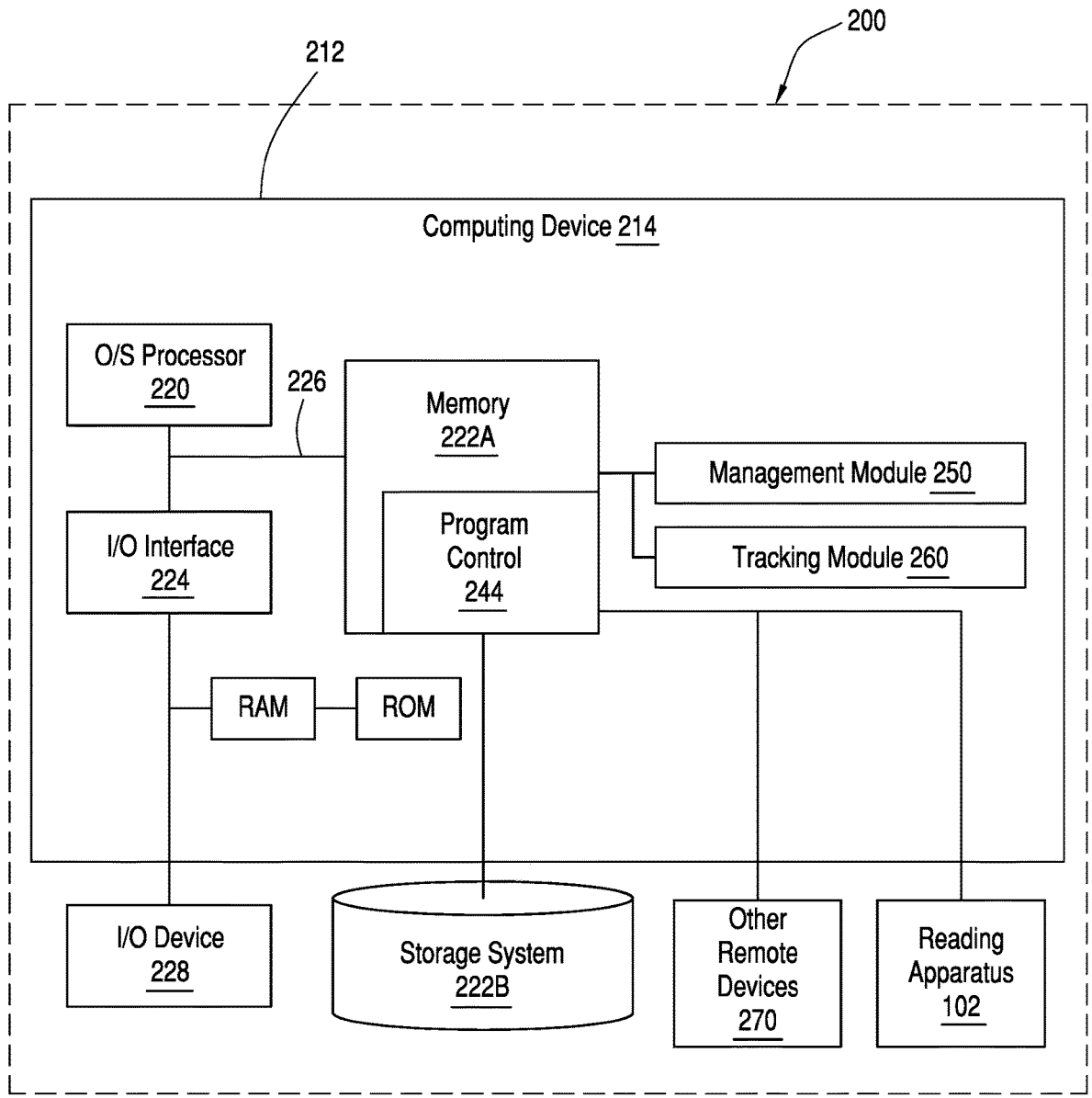
FIG. 3 is an illustrative external environment for implementing the invention in accordance with some aspects of the invention.

FIG. 3 shows an illustrative environment 200 for managing the processes in accordance with the invention. To this extent, the environment 200 includes a server or other computing system 212 that can perform the processes described herein. In particular, the server 212 includes a computing device 214 (e.g., the data manager 104). The computing device 214 can be resident on a network infrastructure or computing device of a third party service provider (any of which is generally represented in FIG. 3).

The computing device 214 also includes a processor 220, memory 222A, an I/O interface 224, and a bus 226. The memory 222A can include local memory employed during actual execution of program code, bulk storage, and cache memories which provide temporary storage of at least some program code in order to reduce the number of times code must be retrieved from bulk storage during execution. In addition, the computing device 214 includes RAM, ROM, and an operating system (O/S).

The computing device 214 may be in communication with an external I/O device/resource 228 and the storage system 222B. For example, the I/O device 228 can comprise any device that enables an individual to interact with the computing device 214 or any device that enables the computing device 214 to communicate with one or more other computing devices using any type of communications link. The external I/O device/resource 228 may be for example, a handheld device, PDA, handset, mechanical keyboard, etc.

In general, the processor 220 executes computer program code (e.g., program control 244), which can be stored in the memory 222A and/or storage system 222B. Moreover, in accordance with aspects of the invention, the program control 244 may communicate with a management module 250, tracking module 260, the reading apparatus 102, and or other remote devices 270 such as an operator's personal computer or mobile device. The management module 250 and tracking module 260 can be implemented as one or more program code in the program control 244 stored in memory 222A as separate or combined modules. Additionally, the management module 250 and tracking module 260 may be implemented as separate dedicated processors or a single or several processors to provide the function of these modules. In embodiments, the management module 250 and tracking module 260 may be configured to carry out the processes of the present invention discussed in further detail herein. While executing the computer program code, the processor 220 can read and/or write data to/from memory 222A, storage system 222B, and/or I/O interface 224. The program code executes the processes of the invention. The bus 226 provides a communications link between each of the components in the computing device 214.

The computing device 214 can comprise any general purpose computing article of manufacture capable of executing computer program code installed thereon (e.g., a personal computer, a smartphone, a laptop, a tablet, etc.). However, it is understood that computing device 214 is only representative of various possible equivalent-computing devices that may perform the processes described herein. To this extent, in some embodiments, the functionality provided by computing device 214 can be implemented by a computing article of manufacture that includes any combination of general and/or specific purpose hardware and/or computer program code. In each embodiment, the program code and hardware can be created using standard programming and engineering techniques, respectively.

Similarly, computing infrastructure 212 is only illustrative of various types of computer infrastructures for implementing the invention. For example, in embodiments, server 212 comprises two or more computing devices (e.g., a server cluster) that communicate over any type of communications link, such as a network, a shared memory, or the like, to perform the process described herein. Further, while performing the processes described herein, one or more computing devices on server 212 can communicate with one or more other computing devices external to server 212 using any type of communications link. The communications link can comprise any combination of wired and/or wireless links; any combination of one or more types of networks (e.g., the Internet, a wide area network, a local area network, a virtual private network, etc.); and/or utilize any combination of transmission techniques and protocols.

Instrument and Cartridge Quality Control Systems

Quality control testing of reagents for laboratory instrumentation has conventionally been performed in the hospital laboratory by skilled technicians. In this model, a technician manually runs a new set of reagents on a given instrument and checks the results to determine if they fall within the expected ranges for a set of control fluids. Where aberrant results are obtained the technician can then check to see if the instrument is at fault, or whether the reagent formulation or assay procedure is the root cause. The skill and experience of the technician generally allows resolution of the problem. In this centralized laboratory model, the skilled technicians and all of the test equipment are located together in a single laboratory and the responsibility of the point-of-care user (phlebotomist, nurse, or physician) is only to draw the blood sample, label it with the correct patient identifier and send it to the laboratory. Essentially all other aspects of the quality system associated with the sample analysis step are laboratory based.

By contrast, the implementation of point-of-care testing systems remote from the hospital laboratory and often remote from the discerning judgment of skilled technical staff creates a novel technical problem for quality assurance of blood testing reagents and devices. Particularly complex single-use integrated devices that contain sensors, reagents, and calibration and/or wash fluids present several issues. Here a robust quality control system and methodology that is efficient and simple to implement by staff not necessarily trained in laboratory methods, e.g. nurses, nurse practitioners and other support staff, is advantageous. Importantly, this should be done while still achieving the same level of quality as in the hospital laboratory. The aforementioned technical solution for centrally managing and implementing a program for quality control compliance achieves these objectives.

A preferred embodiment comprises a method of determining quality compliance for a set of biological sample testing devices, e.g. several hundred or thousands of cartridges of a single type and from a single manufacturing lot. As these may ultimately be used at many different locations throughout the hospital, e.g. Emergency Room and Intensive Care Unit, and with multiple identical or different testing instruments, preferably a network of instruments, the quality control system and methodology should be simple, robust and efficient.

It is standard practice that any given manufacturing lot of devices will have a predetermined expiration date, set either by the manufacturer or the hospital. In the present systems and methods, one or more cartridges are tested using at least one control fluid on a given test instrument. Here the number of cartridges tested and the number and type of control fluids is determined by a (computing device executed) data manager. In some embodiments, the test instrument automatically communicates the quality control cartridge test data to the data manager. The data manager is pre-programmed with an anticipated range of reported target values for each of the control materials, and the data manager determines compliance of the recorded quality control test data with these target values. The data manager then communicates with not only the test instrument from which the results were reported, but the network of identical instruments in the hospital. The communicated message is essentially binary, permitting use before the predetermined expiration date, of the given manufacturing lot of cartridges with any of the instruments in the network when the cartridge test values are in compliance. However, if the results are not in compliance, then the data manager locks out use of these cartridges on the entire network of instruments. Such a method enables multiple different types of test devices from varying manufacturing lots to be efficiently managed in a simple manner compatible with delivery of accurate and timely results at the point-of-care. In preferred embodiments, the communication between the instruments and the data manager is by wireless means, e.g., a WiFi communication protocol.

In another embodiment the systems and methods also comprise obtaining an instrument configuration profile associated with the set of cartridges for a test instrument from a (computing device executed) configuration manager which is part of the data manager. The same general procedure as describe above occurs, but with a specific configuration profile for the cartridge manufacturing lot, cartridge type, or both. Examples of different configurations include sensor coefficients, calibrant fluid analyte values, and sensor response range limits, e.g., anticipated calibrant potential response windows for potentiometric sensors, and anticipated maximum and minimum calibration currents for amperometric sensors, and cell constants for conductimetric sensors.

In another embodiment, it is not necessary that the test instrument be part of a network of instruments, but can operate as a stand-alone system, for example as a single unit at a doctor's office, a nursing home, forward military medical support unit, and ambulance. Again a configuration compliance profile associated with the set of cartridges for the test instrument is obtained from a (computing device executed) configuration manager, e.g., by WiFi. As described previously, the step of performing one or more cartridge tests using at least one control fluid with the instrument is performed and the instrument determines compliance of the test results with test target values based on the instrument configuration profile. Where necessary, the instrument can lock out use of the set of cartridges if the cartridges are not in compliance.

In another embodiment, the systems and methods are illustrated as a series of steps, specifically performing a quality control function for a plurality of wirelessly interconnected blood testing instruments where each instrument can test blood with a plurality of different cartridge types and is interconnected by a data manager. Firstly, receiving a set of cartridges, with a predetermined expiration date, of a single type for use by one or more blood testing instruments. Secondly, performing one or more cartridge tests using at least one control fluid on a selected instrument, or a subset of instruments e.g. three out of a network of twenty or more instruments, where the number or cartridges tested and the number and type of control fluids is determined, scheduled and communicated by the data manager. For example, the selected instrument can in fact comprises two to five instruments as a subset of a network of instruments where the network of instruments is greater than ten instruments. Thirdly, sending the quality control cartridge test data from said instrument to the data manager, wherein the data manager determines compliance of the data with one or more target values. Fourthly, the data manager communicates with the plurality of instruments, permitting use, before the predetermined expiration date, of the set of cartridges with any connected instrument when the set of cartridges are in compliance and not permitting (locking out) use of the set of cartridges with any connected instrument when the set of cartridges are not in compliance.

Those skilled in the art will recognize that it is not only the cartridges that need to be qualified (calibration verification). Other aspects of the present invention are directed to ensuring instruments are qualified independently of the cartridges via the data manager. In another embodiment, this involves a method of performing calibration verification for each of a plurality of wirelessly interconnected blood testing instruments where each instrument can test blood with a plurality of different cartridge types. Typically each instrument is interconnected by the data manager, and the method further involves signaling from the data manager to a selected instrument a requirement for instrument calibration verification. This requires using one or more selected known compliant blood test cartridges with one or more selected control fluids or an electronic simulator. Optionally, this information is displayed as a prompt (with instructions) for the user on the instrument display. Once the user has performed the indicated testing, in some embodiments the instrument communicates the instrument calibration verification test data to the data manager. Thereafter, the data manager, or optionally the instrument, determines compliance of the data with one or more target value, and then communicates with the instrument, permitting use (for a predetermined time period) of the instrument when the calibration verification is in compliance and not permitting (locking out) use of the instrument when the calibration verification is not in compliance.

In preferred embodiments, the data manager schedules the calibration verification for each instrument that is interconnected, e.g. a network of instruments, and optionally provides a replacement or maintenance for an instrument when the calibration verification is not in compliance. The schedule is generally set within an IQCP to be in compliance with a given mandate from a state or country's regulatory body governing laboratory medicine, e.g., CLIA.

Figure 4:
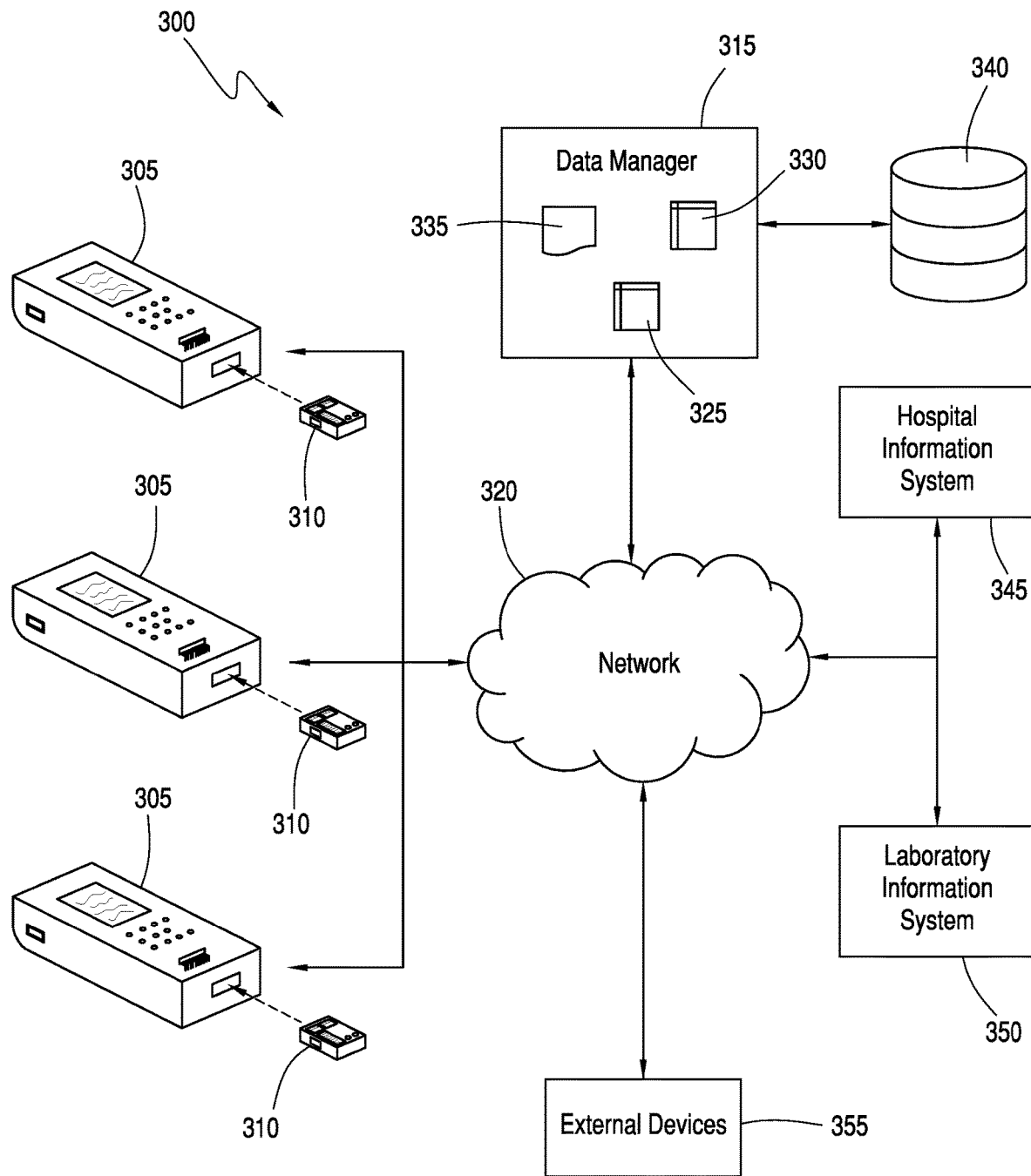
FIG. 4 is a block diagram illustrating a high level architecture of an exemplary quality control system for a point-of-care diagnostic technology, in accordance with some aspects of the invention.

FIG. 4 shows a high level architecture of an exemplary quality control system 300 in accordance with the embodiments of the present invention. The quality control system 300 is configured to ensure that test devices and/or test instruments of a biological sample testing system (e.g., system 100 as discussed with respect to FIG. 1) that are non-compliant with a quality control program are locked out from use on patient samples. The quality control system 300 may be conceived for distributed or point of care analytical testing with a plurality of portable test instruments 305 (e.g., sample testing instrument or reading apparatus 102 as discussed with respect to FIG. 1), typically located in a medical facility. The sample testing instruments 305 are configured to receive one or more devices 310 (e.g., devices 103 or cartridge 120 as discussed with respect to FIGS. 1 and 2, respectively) for purposes of performing one or more analytical tests on a biological sample. Additionally, in accordance with aspects of the present invention, the sample testing instruments 305 are further configured to receive the one or more devices 310 for purposes of performing one or more quality control checks and reporting quality control test data obtained from the quality control checks and quality control process data obtain from internal control processes built into each of the sample testing instruments 305 and the one or more devices 310 that are performed during performance of the one or more quality control checks.

In preferred embodiments, the sample testing instruments 305 are networked based on a client server model in which individual request services and resources from a centralized server such as a data manager 315 (e.g., computing device 214 as discussed with respect to FIG. 3) are communicated over a network 320, such as a local area network, a wide area network, or a wireless device service provider (e.g., a cell phone service provider). In additional or alternative embodiments, the sample testing instruments 305 are networked based on a peer-to-peer network in which interconnected nodes (the sample testing instruments 305) share resources amongst one without the use of a centralized administrative system. The peer-to-peer network may be implemented with a virtual overlay network on top of the network 320, where the nodes in the overlay form a subset of the nodes in the network 320. Data is exchanged directly over the network 320, but at the application layer the nodes are able to communicate with each other directly via logical overlay links each of which corresponds to a path through the network 320.

In accordance with aspects of the client server model, the data manager 315 comprises a configuration manager 325 (e.g., management module 250 as discussed with respect to FIG. 3) and a data tracking system 330 with an operator tracking record 335 (e.g., tracking module 260 as discussed with respect to FIG. 3). The data manager 315 is configured to communicate with and manage the network of sample testing instruments 305 via the network 320. In order to manage the network of sample testing instruments 305, the data manager 315 may be configured to obtain configuration profiles for sample testing instruments 305 and devices 310, distribute attributes for quality control to the sample testing instruments 305 based on one or more IQCPs and/or signal one or more sample testing instruments 305 a requirement for instrument calibration or quality control verification based on one or more IQCPs, receive quality control test data and quality control process data from one or more sample testing instruments 305, determine compliance statuses of the sample testing instruments 305 and devices 310, store the compliance statuses, and distribute the compliance statuses to the sample testing instruments 305.

In preferred embodiments, the configuration manager 325 is configured to develop, modify, implement, and/or monitor one or more quality control programs, e.g., one or more IQCPs. Each type of device 310 (the types of devices are defined by the target analytes that are available for detection using each type of device, e.g., a Chem 8+, Crea, E3+, etc.) may have a specific IQCP because each device is different and presents unique risks. However, a single IQCP could cover multiple tests conducted with the same type of device 310 provided the IQCP factors in the differences unique to each analyte. Each IQCP may be developed by laboratory personnel and/or an administrator in conjunction with the configuration manager 325, or the configuration manager 325 can be configured to automatically select a preloaded IQCP dependent on certain parameters such as a type of device 310 being implemented within the point-of-care system. Development of each IQCP can be implemented via the configuration manager 325 using templates, databases from other computing systems, e.g., LIS or HIS, schedulers, graphical user interfaces, manufacturer's specifications, applicable regulatory and accreditation requirements, and algorithms such as Westgard rules.

Development of the one or more IQCPs can be divided into four steps. The first step involves collecting system information, including manufacturer recommendations on the proper use of devices or assays, the medical application of test results (how test results influence patient management, are test results used for screening versus diagnosis) as this will define performance specifications and allowable tolerance limits for error, and applicable regulatory and accreditation requirements. The second step involves failure modes and effects analysis, which identifies potential sources of failure and determines how such failures affect the point-of-care system. All constituents of the point-of-care system, starting with the patient sample, reagents, environmental conditions that could affect the instruments 305 and the devices 310, the instruments 305 and the devices 310 themselves, and the testing personnel, are considered in the evaluation of possible failures. An estimate of the occurrence of these failures, whether frequent, occasional or remote, as well as the likelihood of harm arising from each failure is determined. The combination of frequency and severity of harm may allow the configuration manager 325 to estimate the criticality or risk of the error.

The third step includes selecting appropriate control measures to detect or prevent the errors, and maintain risk at a clinically acceptable level based on the estimate of the criticality or risk of the error. For example, a common way to monitor the stability of a point-of-care system is through the use of liquid quality control material. The configuration manager 325 can be used to establish ranges and control rules that define how much change in assay performance is allowed before the quality control data are considered out-of-control. Westgard rules are one such example that employ limits calculated from the mean value and standard deviation of control samples measured when the system is stable, and describe when to accept or reject quality control data. In some embodiments, a minimum of two levels of quality control each day of testing may be used. However, the frequency of quality control testing should reflect the point-of-care system risk and be based on the stability of the analyte and the point-of-care system, the presence of built-in controls, the number of patient samples processed, the clinical use of the test results and the frequency of calibration. The frequency of quality control testing should also conform to regulatory and accreditation requirements.

Measurement of quality control samples may be useful in detecting systematic errors that affect all test results in a predictable manner. For example, liquid quality control is effective at detecting errors caused by faulty operator technique (pipette errors or unacceptable movement imparted on the instrument) that affect both patient and quality control samples in the same manner. However, liquid quality control does not address all potential failure modes. Random and unpredictable errors such as hemolysis or lipemia that affect individual samples may be poorly detected by liquid quality control.

For this reason, aspects of the present invention may employ alternative quality control strategies, in addition to the liquid quality control, to ensure that the potential for high risk errors is covered. For example, the instruments 305 and the devices 310 incorporate a variety of biologic and chemical controls and system electronic checks engineered into the test system to address a number of potential errors. Bubbles and clot detection can sense problems with specimen quality and alert the operator with an error code rather than a numerical test result. Further, the devices 310 are consumed in the process of analyzing liquid quality control. Thus, liquid quality control provides little assurance that the next test will perform in the same manner. Such tests include built-in control lines or areas that can detect incorrect test performance and test mishandling or storage degradation with each test. Accordingly, the IQCP may incorporate other control processes that address the risk of errors that are most likely to affect test results such as the quality of the specimen, the reactivity of reagents such as polymerase enzyme, and the temperature cycling of the instruments 305. The other control processes may include, without limitation, programing to: detect specimen errors such as hemolysis, lipemia and icterus, significant differences between the current and previous test results, detection of drift or shift in analyzer performance over time, detection of expired devices 310, detection of instrument 305 orientation and movement, etc.

Once all of the weaknesses in the point-of-care system have been identified and appropriate control processes selected to address each weakness, these hazards and control processes are summarized via the configuration manager 325 as the IQCP having a plurality of attributes. The IQCP is implemented by the data manager 315 using a configuration profile comprising one or more attributes for each instrument 305 and/or device 310, and monitored for effectiveness to ensure that errors are adequately being detected and prevented. The IQCP can be monitored by reviewing quality benchmarks for each instrument 305 and/or device 310 such as operator or physician complaints. When a complaint is received, the configuration manager 325 can be used to troubleshoot and determine what occurred and how to prevent recurrence of the error in the future. The IQCP should be reassessed to determine if this is a new failure not considered during development of the initial IQCP, or whether this is a hazard occurring at higher frequency or with greater severity of harm than previously considered. Once risk is reassessed, the IQCP should be appropriately modified via the configuration manager 325 to maintain risk to a clinically acceptable level, and the modified IQCP is implemented.

In preferred embodiments, the development of the IQCP results in the creation of the plurality of attributes, which are intended to ensure that a right amount and type of quality control is implemented to address a laboratory's or medical care facility's specific risks and ensure quality test results. The plurality of attributes for each IQCP may be configured to identify internal and/or external quality control samples to be used for obtaining the quality control data, thresholds or target values for the control samples, the frequency of using the quality control samples, quality control rules, internal control process checks, technical checks, administrative checks, and corrective action to be taken as a result of invalid quality control data. The internal quality control samples identify control samples provided with devices 310 that have a known reactivity. The external quality control samples identify control samples from an external source that has been validated for use with specific types of the devices 310 and have a known reactivity. The thresholds or target values for the control samples are known values for the reactivity of the control samples and may be provided by the manufacturer of the devices 310 or a third party vendor providing the control samples.

The control samples and corresponding thresholds or target values can be selected by the data manager 315 or a primary user. For example, the data manager 315 can be configured to automatically select control samples and corresponding thresholds or target values based on control samples that ship with each manufacturing lot of devices 310 or control samples that are recommended by a manufacturer of the devices 310 for quality control of the devices 310. Optionally, the primary user can be a point-of-care coordinator who operates the data manager 315 to manually select or input control samples and corresponding thresholds or target values based on similar information and/or additional information such as information pertaining to external controls preferred by a point-of-care facility. The thresholds or target values can be for incoming quality control, intermittent quality control, and/or daily quality control. The thresholds or target values can be selected by the data manager 315 or the primary user for each IQCP, each type of device 310, each manufacturing lot of devices 310, each instrument 305 or a subset of instruments 305, etc.

The frequency of use can be defined based on temporal, process, or environmental conditions such as a minimum number of times per day, a minimum number of times per week and a preferred time of the week for testing, upon a new shipment of devices 310, upon starting use of a new manufacturer's lot number of devices 310, if environmental conditions exceed a range for stability of devices 310, etc. Preferably, the quality control system 300 is designed with the data manager 315 having the functionality of a scheduler that accommodates IQCP based, device type based, lot based, and/or instrument based scheduling of performance of quality control. For example, schedule requirements may be customizable for each IQCP, cartridge type, manufacturer's lot, instrument, and/or subset of instruments. Specifically, the quality control fluids/levels to be run and the maximum period between quality control events may be defined, e.g., automatically using predefined templates or in a selection menu. The lot-based feature accommodates separate requirements for initial lot acceptance (incoming quality control) and for scheduled (daily quality control) quality control. This feature can also accommodate the recording of selected or predetermined lot-acceptance information. Credit for passed quality control runs may be shared with all instruments 305, and cartridge lot lockout could be configured to apply to all instruments 305 in the network. Generally, it may be preferred that a specific instrument (or subset of instruments 305) that is used for the quality control testing be changed from run to run, and thus such a feature could also be defined within the scheduler (e.g., an identifier for a given instrument or identifiers for instruments within a subset of instruments can be included as an attribute for performing the quality control). Although, it is also contemplated by the present invention that a same or randomly selected instrument 305 or subset of instruments 305 may be used for all quality control testing.

The quality control rules are a decision criterion for judging whether an analytical run is in-control or out-of-control, e.g., Westgard Rules, and may include utilizing one or more of the following: the thresholds or target values for the control samples, the mean or average of quality control data, the standard deviation for the quality control data, the coefficient of variation, a standard deviation index, a median of quality control data, a mode of quality control data, a range of quality control data, a normal or Gaussian distribution of the quality control data, and Levy-Jennings Charts, to determine a compliance status of each of the instruments 305 and each manufacturer's lot of devices 310. For example, in some embodiments the configuration manager 325 may be configured to plot the manufacturer quality control mean and standard deviation at the beginning of a new lot, e.g., the thresholds or target values for the control samples, update the mean and standard deviation values after accumulating minimum number of quality control points of data, determine flags or invalidity of quality control data when a quality control rule is violated and/or the thresholds or target values are exceeded, and generate exception or exclusion logs or reports such as compliance status reports for each manufacture's lot of the devices 310 or each instrument 305.

The internal control process checks may include checks for biologic and chemical controls and system electronic checks that may be used to detect incorrect test performance and test mishandling or storage degradation. For example, the internal control process checks may be configured to check for specimen errors such as hemolysis, lipemia and icterus, significant differences between the current and previous test results, detection of drift or shift in analyzer performance over time, detection of expired devices 310, detection of instrument 305 orientation and movement, detection of bubbles or clots within the sample, etc. In preferred embodiments, the predetermined expiration date of devices 310 can by selected by the data manager 315 or a primary user. For example, the data manager 315 can be configured to automatically select a predetermined expiration date based on information provided by the manufacturer for each manufacturing lot of devices 310. Optionally, the primary user can be a point-of-care coordinator who operates the data manager 315 to manually select or input a predetermined expiration date based on similar information and/or additional information such as information pertaining to shipping conditions that may have affected the predetermined expiration date. In some embodiments, the predetermined expiration date may be a modified expiration date based on environmental conditions that each device may have been exposed to such as refrigerated and/or ambient temperature shelf life (see, e.g., U.S. Pat. No. 7,552,071, which is incorporate herein in its entirety). The expiration of the devices 310 based on the predetermined expiration date and/or the modified expiration date can be determined by the instruments 305/devices 310 and reported to the data manager 315 as a portion of the quality control process data.

The technical checks may include checks for correlation and delta checks. For example, the technical checks may be configured to check whether the analytical results fall within one or more sets of action ranges or reference ranges, whether multiple analytical test results correlate, whether the analytical test results correlate with clinical diagnosis, whether the analytical results fall outside of certain clinically significant limits or critical values, and whether the analytical results are impossible or incompatible with normal ranges of the analytical test. In preferred embodiments, a calibration verification (Cal Ver) technical feature includes auto pass/fail functionality to a known quality control auto pass/fail feature, which acts as part of an advanced quality control baseline for a given IQCP. For example, the Cal Ver may include delta drift and verification methodology (see, e.g., U.S. Pat. No. 5,112,455, which is incorporated herein in its entirety).

In additional or alternative embodiments, customizable action ranges may be implemented in accordance with aspects of the present invention. Unlike conventional systems, which only exhibit a single set of action ranges and a single set of reference ranges for a given analyte, the present invention extends the functionality of action ranges and reference ranges by providing multiple sets of ranges applicable to different sample types, patient ages, and genders as defined in the configuration profile developed and/or provided by the configuration manager 325. For example, multiple (e.g., five) action ranges for some analytes, e.g., creatinine, may be defined in the configuration profile where the ranges are based on patient age. It is well established that several analytes that are commonly measured in blood have different reference ranges for various sub-populations, for example those based on age, gender and race.

The administrative checks may include checks for reporting results, checks for flagging of abnormal results, checks for test completion, and checks for quality control and maintenance record upkeep. In preferred embodiments, customized critical results and/or critical tests may be designated and reported in accordance with attributes of the IQCP. As described herein, a critical result and/or critical test is a result and/or test that always requires rapid communication of the results to the user, e.g., physician. In the instance of a critical result, the results are rapidly communicated as critical if within a specified critical range, whereas in the instance of a critical test, the results are rapidly communicated independent of whether the results are normal or abnormal. In the traditional central laboratory model, the laboratory manager is responsible for ensuring identified critical results and tests are reported within a certain time period. The attributes of the present invention may be configured to define an acceptable length of time between the ordering of a test or critical test and the receipt of that the critical result or result of the critical test by the responsible licensed caregiver. Additionally, where cartridge lots are in quality control compliance, any test run on the system permits users to designate that specific test as a "critical test" to assure immediate notification of licensed responsible caregiver for all results, via the instrument display or across the network of instruments 305. The data manager is 315 is also configured to check on whether the reporting and designation of critical results and tests are implemented in accordance with the attributes defined for a given IQCP. The present invention also allows the data manager 315 to define attributes that identify critical results and tests based on a location in which the analytical test is performed within the point-of-care facility. For example, the data manager 315 can be used to define attributes that identify critical results and tests that are not specific or independent of the location in which they are performed, or a specific or dependent of the location in which they are performed, e.g., critical care but not the emergency room.

In additional or alternative embodiments, the critical results or results of critical tests may be displayed on one or more instruments 305 using graphical features, e.g., colored borders and icons adjacent to a given result on the instrument display. This feature acts to provide a mechanism to capture a complete electronic record of critical result and test notifications and log the notifications on the data manager 315 (e.g., saved with data store 340) for future reference as part of the overall quality control system. This feature also ensures that regulatory requirements for reporting are met with minimal burden for operators and compliance risk for point-of-care testing is reduced for the point-of-care facility. For example, the logging the critical result or test notifications provides a facility-customizable electronic form to all test records that contain critical result or critical test. The electronic form can be customized to include additional data (beyond the standard test record elements) to ensure that a complete record of physician notification is captured, e.g., responsible caregiver, time of notification, etc. The electronic form may include specified fields in the post-result accessible as pages from the data manager 315 and, optionally, on the display screen of individual instruments 305. Additional optional administrative check features include, auto-order capture, auto-prompt for notification, integrated timers/warnings, track performance metrics, user competency tracking and de-certification, notification of other users of non-compliance and electronic notification and confirmation, etc.

The corrective action to be taken as a result of invalid quality control data may include repeating the quality control test(s), assumption of a problem with the instrument 305, the devices 310, the internal/external control samples, or an operator of the instrument 305, disabling the instrument 305 from performing further analytical testing, which may be device 310 dependent or independent, continuation of analytical testing with an alternative testing algorithm, diagnosing and identifying the cause of the problem, requesting maintenance or replacement of the instrument 305, reporting problems to supervisory personnel or administrators of the point-of-care quality control system, identifying procedures to take corrective action, etc. In preferred embodiments, a manufacturer's lot based quality control and corrective action approach may be established such that a manufacturer's lot for a type of device is locked out from all instruments 305 within the network if the quality control attributes of the IQCP for the type of device 310 are not met or non-compliant, e.g., quality control tests are not performed in accordance with a defined schedule, quality control data is not within thresholds or target values identified or set for control samples, quality control data fails one or more quality control checks, quality control process data does not satisfy one or more internal process control checks, technical checks, or administrative checks, etc.

In preferred embodiments, the data tracking system 330 includes an operator tracking record 335 (e.g., tracking module 260 as discussed with respect to FIG. 3) and may be in communication with the data store 340 (e.g., one or more databases stored in a memory such as storage system 222B or memory 222A as discussed with respect to FIG. 3). Additionally, the data tracking system can communicate in a mono-directional or bi-directional manner with devices internal to the system 300 including the instruments 305, HIS 345, and LIS 350, and other devices 355 external to the system 300 (e.g., external computing devices that could send data to the data tracking system 330, such as a personal computing device or terminal within a facility). Operator information for each instrument 305 may be maintained and stored within the operator tracking record 355 and/or the data store 340. The operator information may include the identification of operators authorized to perform analytical tests within the point-of-care system using instruments 305 and devices 310, the identification of operators who performed quality control tests, the classification of operators as either compliant or non-compliant with present competency testing for instruments 305 and/or devices 310, and the identification of operators that performed operations or analytical testing on each instrument 305.

The plurality of attributes for each IQCP (e.g., internal and/or external quality control samples, thresholds or target values for the control samples, the frequency of using the quality control samples, quality control rules, etc.) may be stored in the data store 340. One or more of the attributes (e.g., the identification of internal and/or external quality control samples, the thresholds or target values for the control samples, and the frequency of using the quality control samples) for each IQCP may be selected by the data manager 315 or an administrator such as quality compliance manager to generate the configuration profile, which is communicated from the data tracking system 330 to the instruments 305 to initiate compliance with a given IQCP.

Subsequently, quality control data and quality control process data generated in response to the one or more attributes may be communicated from the instruments 305 to the configuration manager 325 and/or the data tracking system 330. The quality control data and quality control process data can be stored in the data store 340. In circumstances of compliance with the IQCP, the data manager 315 may permit use of at least one of the instruments 305 and/or use of at least one device 310 with the instruments 305, whereas non-compliance may automatically lock out use on at least one of the instruments 305 and/or use of at least one device 310 with the instruments 305. The compliance or non-compliance status of each instrument 305 and/or each device 310 may be stored in the data store 340.

In preferred embodiments, the configuration manager 325 is configured to generate an instrument configuration profile associated with a set of devices 310 (e.g., a manufacturing lot of devices), and after running select control samples, the quality control data is communicated to the data manager 315 and the data manager 315 determines compliance of the quality control data with the thresholds or target values for the control samples in the instrument configuration profile. The data manager 315 then communicates with not only the test instrument 305 from which the quality control data were communicated, but the network of instruments 305. The communicated message permits use before the predetermined expiration date, of the set of devices 310 with any of the instruments 305 in the network when the quality control data is in compliance. However, if the quality control data is not in compliance, then the message locks out use of the set of devices 310 on the entire network of instruments 305.

Alternatively, the configuration manager 325 is configured to provide an instrument configuration profile associated with a set of devices 310 (e.g., a manufacturing lot of devices), and after running select control samples, the instrument 305 determines compliance of the quality control data with the thresholds or target values for the control samples in the instrument configuration profile. The instrument 305 then permits use before the predetermined expiration date, of the set of devices 310 with the instruments 305 when the quality control data is in compliance. However, if the quality control data is not in compliance, then the instrument 305 locks out use of the set of devices 310 on the instrument 305. Additionally, the instrument 305 communicates with the network of instruments 305. The communicated message permits use before the predetermined expiration date, of the set of devices 310 with any of the instruments 305 in the network when the quality control data is in compliance. However, if the quality control data is not in compliance, then the message locks out use of the set of devices 310 on the entire network of instruments 305.

Instrument and Cartridge Quality Control Methods

FIGS. 5-8 show exemplary flowcharts for performing the process steps of the present invention. The steps of FIGS. 5-8 may be implemented using the computing devices and systems described above with respect to FIGS. 1-4. Specifically, the flowcharts in FIGS. 5-8 illustrate the architecture, functionality, and operation of possible implementations of the systems, methods and computer program products according to several embodiments of the present invention. In this regard, each block in the flowcharts may represent a module, segment, or portion of code, which comprises one or more executable instructions for implementing the specified logical function(s). It should also be noted that, in some alternative implementations, the functions noted in the blocks may occur out of the order noted in the figure. For example, two blocks shown in succession may, in fact, be executed substantially concurrently, or the blocks may sometimes be executed in the reverse order, depending upon the functionality involved. It will also be noted that each block of the flowchart illustrations, and combinations of blocks in the flowchart illustrations, can be implemented by special purpose hardware-based systems that perform the specified functions or acts, or combinations of special purpose hardware and computer instructions.

Figure 5:
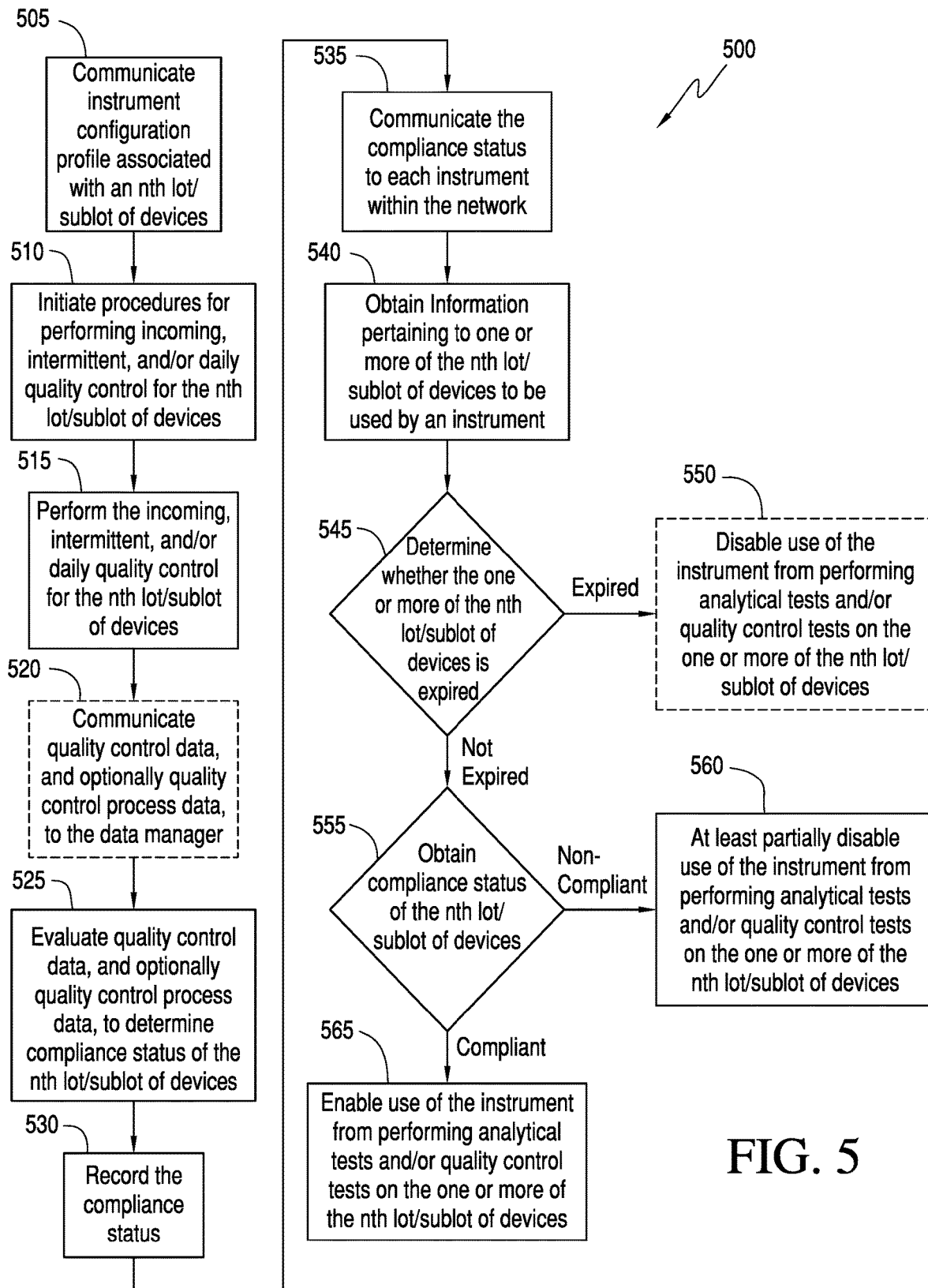
FIGS. 5-8 are illustrative process flow diagrams for implementing the system in accordance with some aspects of the invention.

In one embodiment of the present invention, the computing devices and systems described above may be configured to perform incoming, intermittent, and/or daily lot based quality control for one or more devices in accordance with one or more IQCPs. As shown in FIG. 5, a process 500 may be provided for performing incoming, intermittent, and/or daily quality control for an nth lot/sublot of devices. At step 505, an instrument configuration profile associated with the nth lot/sublot of devices (e.g., devices 310 as described with respect to FIG. 4) is communicated from a data manager (e.g., data manager 315 as described with respect to FIG. 4) to one or more computing devices to initiate the incoming, intermittent, and/or daily quality control of the nth lot/sublot of devices. In preferred embodiments, the instrument configuration profile may be communicated from the data manager to at least one of: all instruments (e.g., instruments 305 as described with respect to FIG. 4) in a network, a defined instrument or subset of instruments in a network (e.g., defined via the attributes), a randomly selected instrument or subset of instruments in a network, one or more terminals of the HIS or LIS, and one or more external devices associated with users of the nth lot/sublot of devices. The instrument configuration profile includes instructions on how to perform quality control in compliance with the one or more IQCPs. For example, the instrument configuration profile may include the identification of internal and/or external quality control samples to be run on the nth lot/sublot of devices, the thresholds or target values for the control samples, and/or the frequency of performing the quality control.

At step 510, the instrument configuration profile is configured to initiate procedures for performing the incoming, intermittent, and/or daily quality control for the nth lot/sublot of devices. In preferred embodiments, the initiation procedure includes displaying a request for performance of quality control on a display of the one or more computing devices in accordance with the instrument configuration profile. In additional or alternative embodiments, the initiation procedure includes providing an indicator for quality control such as a blinking light emitting diode, displaying a graphical indicator on the display of the one or more computing devices, and/or sending a message to an operator of the one or more computing devices such (e.g., an email or text message to an external device of the operator). In any event, the procedures for performing the quality control may be triggered based on events and/or a calendar as defined within the instrument configuration profile. For example, a request for incoming quality control may be triggered upon receiving the nth lot/sublot of devices at a central laboratory from a manufacturer or receiving the nth lot/sublot of devices at a point-of-care location within a medical care facility. Alternatively, a request for intermittent quality control may be triggered upon powering on one or more instruments or intermittently selecting one or more instruments to perform the quality control. Alternatively, a request for daily quality control may be triggered upon insertion of a device from the nth lot/sublot of devices into the one or more instruments for the first time in a day or at a specified time within the day such as 8 am.

At step 515, the incoming, intermittent, and/or daily quality control is performed for the nth lot/sublot of devices in accordance with the instrument configuration profile. In preferred embodiments, the performance of the incoming, intermittent, and/or daily quality control includes optionally determining an expiration date of the nth lot/sublot of devices (see, e.g., U.S. Patent Application Publication No. 2013/0002279 and U.S. Pat. No. 7,552,071, which are incorporated herein in their entireties) and/or performing one or more quality control tests by running one or more quality control samples defined within the instrument configuration profile on one or more of the nth lot/sublot of devices in order to detect one or more target analytes within the one or more quality control samples. The performance of the one or more quality control tests may be executed using the one or more instruments within the network as defined via the instrument configuration profile (e.g., the one or more instruments to which the instrument configuration profile was communicated). Alternatively, in instances in which the instrument configuration profile does not define which of the instruments to use for performing the one or more quality control test, then the one or more quality control tests may be performed on any of the instruments within the network capable of performing the quality control tests.

In additional or alternative embodiments, the performance of the incoming, intermittent, and/or daily quality control includes performing one or more tasks other than performing the quality control tests. The performance of the one or more tasks may be executed using the one or more instruments (e.g., as defined by the instrument configuration profile), the one or more terminals of the HIS or LIS, and/or the one or more external devices. For example, the one or more IQCPs may be developed to include attributes for incoming quality control that include visual inspection tasks of the nth lot/sublot of devices such as visually inspecting the number of the nth lot/sublot of devices received, visually inspecting the integrity of the nth lot/sublot of devices (e.g., is the packaging compromised such that the devices are damaged or exposed), and visually inspecting the expiration date of the nth lot/sublot of devices. Upon the visual inspection, the results of the visual inspection may be evaluated and recorded using the one or more instruments, the one or more terminals of the HIS or LIS, and/or the one or more external devices.

Optionally at step 520, quality control data, and optionally quality control process data, obtained from the performance of the incoming, intermittent, and/or daily quality control is communicated to the data manager. The quality control data includes the results of the incoming, intermittent, and/or daily quality control performed using the one or more instruments, the one or more terminals of the HIS or LIS, and/or the one or more external devices such as an expiration date of the nth lot/sublot of devices, the quality control test results, and the results of the visual inspection the nth lot/sublot of devices. The quality control process data includes results from a variety of biologic and chemical controls and system electronic checks engineered into the instruments and/or the devices to address a number of potential errors, e.g., the determination of bubbles in a quality control sample.

At step 525, the quality control data, and optionally the quality control process data, is evaluated to determine a compliance status of the nth lot/sublot of devices with the plurality of attributes of the IQCP. For example, the evaluation may include comparing the quality control test results with the thresholds or target values for the control samples, and optionally control rules such as Westgard Rules, comparing a predetermined expiration date or a modified expiration date with a current date, comparing a number of the nth lot/sublot of devices received with a number of the nth lot/sublot of devices ordered or anticipated in the delivery, comparing a number of packages of the nth lot/sublot of devices that are damaged to an acceptable amount of damaged packages, and comparing temporal, process, and/or environmental conditions to a schedule or acceptable conditions. If it is determined that the quality control data, and optionally the quality control process data, comply with the attributes of the configuration profile and/or the IQCP, then the status of the nth lot/sublot of devices is recorded as compliant. For example, in an instance where the quality control test results are within the thresholds or target values for the control samples and the nth lot/sublot of devices are not expired, then the status of the nth lot/sublot of devices may be recorded to indicate a compliant status. However, if it is determined that the quality control data, and optionally the quality control process data, do not comply with the plurality of attributes of the IQCP, then the status of the nth lot/sublot of devices is recorded as non-compliant. For example, in an instance where the quality control test results are outside the thresholds or target values for the control samples and the nth lot/sublot of devices are not expired, then the status of the nth lot/sublot of devices may be recorded to indicate a non-compliant status. Alternatively, in an instance where the quality control test results are within the thresholds or target values for the control samples but the nth lot/sublot of devices are expired, then the status of the nth lot/sublot of devices may be updated to indicate a non-compliant status.

In preferred embodiments, the quality control data, and optionally quality control process data, is communicated to the data manager at step 520 and the data manager evaluates the quality control data, and optionally quality control process data to determine the compliance status of the nth lot/sublot of devices with the plurality of attributes of the IQCP. In alternative or additional embodiments, the one or more instruments that performed the incoming, intermittent, and/or daily quality control evaluates the quality control data, and optionally quality control process data to determine the compliance status of the nth lot/sublot of devices with the plurality of attributes of the IQCP.

As should be understood, the determination of the compliance status could be, but need not be, an all or nothing evaluation where a non-compliance status is determined whenever there is non-compliance with at least one of the plurality of attributes. Instead, compliance with the attributes can be evaluated holistically by the data manager, the instrument, and/or a user, e.g., an administrator, to make a final determination on whether the nth lot/sublot of devices should receive a compliant or non-compliant status. For example, in an instance where the quality control test results are within the thresholds or target values for the control samples and the nth lot/sublot of devices are not expired but the number of the nth lot/sublot of devices received does not match the number of the nth lot/sublot of devices ordered or anticipated in the delivery, then a status of the nth lot/sublot of devices may be updated to indicate a compliant status regardless of the shortage or surplus of the nth lot/sublot of devices. Additionally, in an instance where the quality control test results are within the thresholds or target values for the control samples and the nth lot/sublot of devices are not expired but the nth lot/sublot of devices were delivered at ambient temperature rather than refrigerated temperature, then a status of the nth lot/sublot of devices may be updated to indicate a compliant status regardless of the shipping environment conditions.

Furthermore it should be understood, the determination of the compliance status could be, but need not be, a definitive compliant or non-compliant status. Instead, compliance or non-compliance with the attributes can be changed or updated by data manager, the instrument, and/or a user in view of corrective action and/or newly obtained quality control data, and optionally quality control process data. For example, in an instance where the quality control test results are outside the thresholds or target values for the control samples and the nth lot/sublot of devices are not expired but the quality control process data indicates that bubbles were present during the quality control test, then a status of the nth lot/sublot of devices may be updated to indicate a non-compliant status. However, the data manager, the instrument, and/or a user may also be configured to implement corrective action as a result of the invalid quality control data such as requesting the quality control test(s) be repeated while taking steps to alleviate bubble formation (e.g., reduce or prevent inappropriate movement of the instrument during testing). Thereafter, if the quality control test results are now within the thresholds or target values for the control samples and the nth lot/sublot of devices are not expired, then a status of the nth lot/sublot of devices may be updated to indicate a compliant status.

Although steps 515-525 are directed to instance in which the incoming, intermittent, and/or daily quality control is performed for the nth lot/sublot of devices, it should be understood that instances in which the incoming, intermittent, and/or daily quality control is not performed are also contemplated by the present invention. For example, in instances in which the incoming, intermittent, and/or daily quality control is not performed in response to the instrument configuration profile and/or the schedule of the incoming, intermittent, and/or daily quality control, the data manager or the one or more instruments are configured to determine the compliance status of the nth lot/sublot of devices as non-compliant. The determination of non-compliant may be based on the absence of the quality control data, and optionally the quality control process data, after a period of time in which it is expected that the quality control data, and optionally the quality control process data, should have been generated and/or received in response to the instrument configuration profile and/or the schedule of the incoming, intermittent, and/or daily quality control.

At step 530, the determined compliance status of the nth lot/sublot of devices is recorded. In preferred embodiments, the determined compliance status of the nth lot/sublot of devices is recorded or stored in a data table, e.g., a database, stored in memory of the data manager or the one or more instruments that performed the incoming, intermittent, and/or daily quality control. In additional or alternative embodiments, the data table may be stored in a data table stored in data store, e.g., data store 345 discussed with respect to FIG. 4, external to the data manager or the one or more instruments. As should be understood by those of ordinary skill in the art, the data table may be configured to include any number and type of devices with corresponding lot numbers and compliance statuses beyond just the nth lot/sublot of devices such that the data table maintains a real time persistent record of the compliance status of all devices available for use throughout a point-of-care facility.

At step 535, the compliance status of the nth lot/sublot of devices is communicated to each instrument within the network of instruments. In preferred embodiments, the compliance status of the nth lot/sublot of devices is communicated to each instrument within the network of instruments from the data manager. In alternative or additional embodiments, the compliance status of the nth lot/sublot of devices is communicated to each instrument within the network of instruments from the one or more instruments that performed the incoming, intermittent, and/or daily quality control (e.g., peer-to-peer). Thus, not only do the one or more instruments that performed the incoming, intermittent, and/or daily quality control know the compliance status of the nth lot/sublot of devices, but each instrument within the network of instruments knows the compliance status of the nth lot/sublot of devices.

The compliance status of the nth lot/sublot of devices is communicated to each instrument by sending the data table as a part of the message or data packet communicated to the instruments within the network. Once the message or data packet is received by the instruments, the data table with the determined compliance status is stored in memory of the instruments such that the instruments are continually capable of obtaining the compliance status of all devices available for use throughout a point-of-care facility.

In instances in which the compliance status of the nth lot/sublot of devices is non-compliant, the message communicated to the instruments may further include corrective action that may be taken to possibly correct the failed quality control data. For example, the message may include instructions to repeat the quality control tests, take a predetermined action such as placing the instrument on a solid surface during testing, using a different set of control samples, perform a power cycle of the instrument, perform calibration of the instrument, etc. Additionally, in instances in which the compliance status of the nth lot/sublot of devices is non-compliant, an additional message may be communicated from the data manager or the instrument to another computing system or device, e.g., an external device such as an inventory control system, a computing terminal of the administrator or laboratory personnel, and/or a computing device of maintenance personnel. The additional message may prompt or automatically trigger the replacement of the nth lot/sublot of devices with another lot/sublot of devices either through an order being placed to the manufacturer or replacement using internal inventory, as disclosed in, for example, U.S. Pat. No. 7,552,071. In some embodiments, the additional message may alternatively or additionally prompt or automatically trigger a request for maintenance or replacement of the instrument. In accordance with aspects of the present invention, the corrective action and additional messages may be generated manually or triggered automatically in accordance with the compliance or non-compliance of the quality control data, and optionally the quality control process data, with the attributes of the configuration profile and/or the IQCP. For example, non-compliance with the expiration date of the nth lot/sublot of devices may prompt or trigger the replacement of the nth lot/sublot of devices whereas non-compliance with a proper thermal cycling of the instrument could be configured to prompt or trigger the request for maintenance or replacement of the instrument.

At step 540, an instrument from the network of instruments obtains information pertaining to one or more of the nth lot/sublot of devices that are intended to be used in conjunction with the instrument for performing an analytical test on a patient sample and/or performing another quality control test on one or more quality control samples. For example, the devices or boxes of the nth lot/sublot of devices include one or more encoding arrangements configured to convey the information to the instrument. More specifically, the various encoding arrangements are configured to convey relevant information to the instrument, for example, the identity of a specific device type, date and location of manufacture, manufacturing lot number, the predetermined or modified expiration date, a unique number associated with a device, coefficients for use by the invention associated with the calculation of blood or other sample parameters and the like.

In preferred embodiments, the one or more encoding arrangements can be based upon binary coding pin arrays of the types disclosed in, for example, U.S. Pat. No. 4,954,087 and U.S. Provisional Patent Application No. 62/055,922, which are incorporated herein in their entireties. For example, the resistance of a resistor may be measured by a detector (e.g., processor) by applying a small voltage, e.g., 1 mV, between at least two pins, subsequent to (e.g., immediately after) the device being inserted into the instrument. The value of the measured resistance can then be used by the instrument for cartridge and/or lot identification. For example, each cartridge type (e.g., i-STAT® cartridges EC8+, CG8+, EG7+, CHEM8+, etc.) and/or lot of cartridges may be associated with a certain resistance or resistance range such that a measured resistance of the cartridge may be used to identify the type and/or lot of the cartridge using a look-up table.

In additional or alternative embodiments, the one or more encoding arrangements can be based upon a barcode such as a patient's bar-coded wristband, a barcode on the device, or from any other item such as a box of the nth lot/sublot of devices, and either alternatively or in addition to the barcode, a radio-frequency (RF) tag that is contained on or in each device or each box of devices, as disclosed in, for example, U.S. Pat. No. 7,552,071. For example, each device or box of devices can have a code, such as for example, a bar code, RF tag, or the like, associated with the device or box of devices. When the device or box of devices are going to be used in conjunction with the instrument for performing the analytical test or another quality control test, the code associated with the device or box of devices can be conveyed to the instrument via an identification device associated with the instrument (e.g., via a barcode reader, an RF reader, or the like).

Optionally at step 545, the instrument from the network of instruments determines whether the one or more of the nth lot/sublot of devices are expired. For example, the instrument may be configured to compare the predetermined or modified expiration date obtained in step 540 to a present time maintained or obtained via a processor within the instrument to determine whether the predetermined or modified expiration date has been elapsed. Additionally, or alternatively, the instrument may be configured to determine the expiration of the one or more of the nth lot/sublot of devices based on a time-temperature indicator such as time-temperature sensing circuitry, as disclosed in, for example, U.S. Pat. No. 7,552,071.

Optionally at step 550, when the one or more of the nth lot/sublot of devices are determined to be expired, the instrument is disabled from performing the analytical test and/or the another quality control test. For example, if an ambient or room temperature expiration date or timing has elapsed, then the instrument locks out the expired devices. Because the expired devices are locked out, the expired devices are not used. Thus, exemplary embodiments of the present invention can prevent devices from being used that have expired.

At step 555, when the one or more of the nth lot/sublot of devices are determined not to be expired, or in embodiments in which the instrument does not perform step 545 to determine whether the one or more of the nth lot/sublot of devices are expired, the instrument from the network of instruments obtains the determined compliance status of the one or more of the nth lot/sublot of devices that are intended to be used in conjunction with the instrument for performing an analytical test and/or another quality control test. For example, the instrument is configured to use the information pertaining to the devices obtained in step 540 to look up the compliance status of the devices in the data table stored in step 530.

At step 560, when the compliance status of the one or more of the nth lot/sublot of devices is compliant, the instrument is configured to operate under normal operating procedures in order to perform the analytical test and/or the another quality control test using the one or more of the nth lot/sublot of devices. For example, insertion of the one or more of the nth lot/sublot of devices into the instrument and the confirmation of the compliant quality control compliance status executes program instructions that operate a mechanism such as a pump to apply pressure to an air-bladder forcing air through one or more conduits of the one or more of the nth lot/sublot of devices to move a metered portion of the patient sample or the quality control sample, that is optionally amended with a compound or compounds present initially as a dry coating on an inner surface of the one or more conduits, into contact with an analyte sensor or sensors located within a detection region of the one or more conduits. Thereafter, electrical signals generated from the detection of target analyte at the analyte sensor or sensors are transmitted from the one or more of the nth lot/sublot of devices to the instrument, where program instructions are executed to interpret the electrical signals and provide, e.g., display and/or report, a result(s) of the analytical test and/or the another quality control test.

At step 565, when the compliance status of the one or more of the nth lot/sublot of devices is non-compliant, the instrument is configured to be at least partially disabled from performing the analytical test and/or the another quality control test. In accordance with aspects of the present invention, the at least partial disabling of the instrument can be implemented using a number of mechanisms and does not necessarily mean that the instrument does not operate and run the analytical test and/or the another quality control test. For example, in some embodiments, the instrument may be prevented from initiating performance of the analytical test and/or the another quality control test using the one or more of the nth lot/sublot of devices such that the analytical test and/or the another quality control test are not run using the inserted device and the inserted device is not exhausted (i.e., the instrument is completely disabled from performing the analytical test and/or the another quality control test). However, in preferred embodiments, the instrument may run the analytical test and/or the another quality control test but instead of providing the results of the analytical test and/or the another quality control test in accordance with the normal operation of the instrument, the instrument is configured to provide, e.g., display and/or report, an error message, e.g., the lot number and/or type of device has failed quality control (i.e., the instrument is partially disabled from performing the one or more analytical test). This mechanism would effectively prevent reporting of the results to the operator and/or the health care team.

In alternative embodiments, if the compliance status of the device is non-compliant, the instrument may be configured to run the one or more analytical tests and provide, e.g., display and/or report, the results of the one or more analytical tests. However, the display and/or reporting of the results includes a flag or some manner of indicating that the lot number and/or type of device has failed quality control. The flag may be configured to provide details on the failed quality control including the attributes of the IQCP that are not in compliance. In some embodiments, the details on the failed quality control may also include corrective action that may be taken to possibly correct the failed quality control.

The advantage of the aforementioned technical solution for centrally managing and implementing IQCP for quality control compliance is that it will eliminate the technical problems of having to perform a default frequency of two levels of quality control each day on each unit-use test device with liquid quality control and an inability to balance the default frequency of two levels of quality control with unit-use test devices that include internal control systems and processes built into each unit-use test device. For example, implementation of the steps of FIG. 5 using the computing devices and systems described above with respect to FIGS. 1-4 provide a technical contribution over conventional quality control systems and methods because the technical features of the present invention interoperate to enable or disable use of a set or lot of testing devices by some (e.g., a subset) or all of the instruments in a network based on a plurality of attributes using a centralized computing environment to ensure quality across the network of instruments and strike the right balance of liquid quality control in concert with internal control processes.

Figure 6:
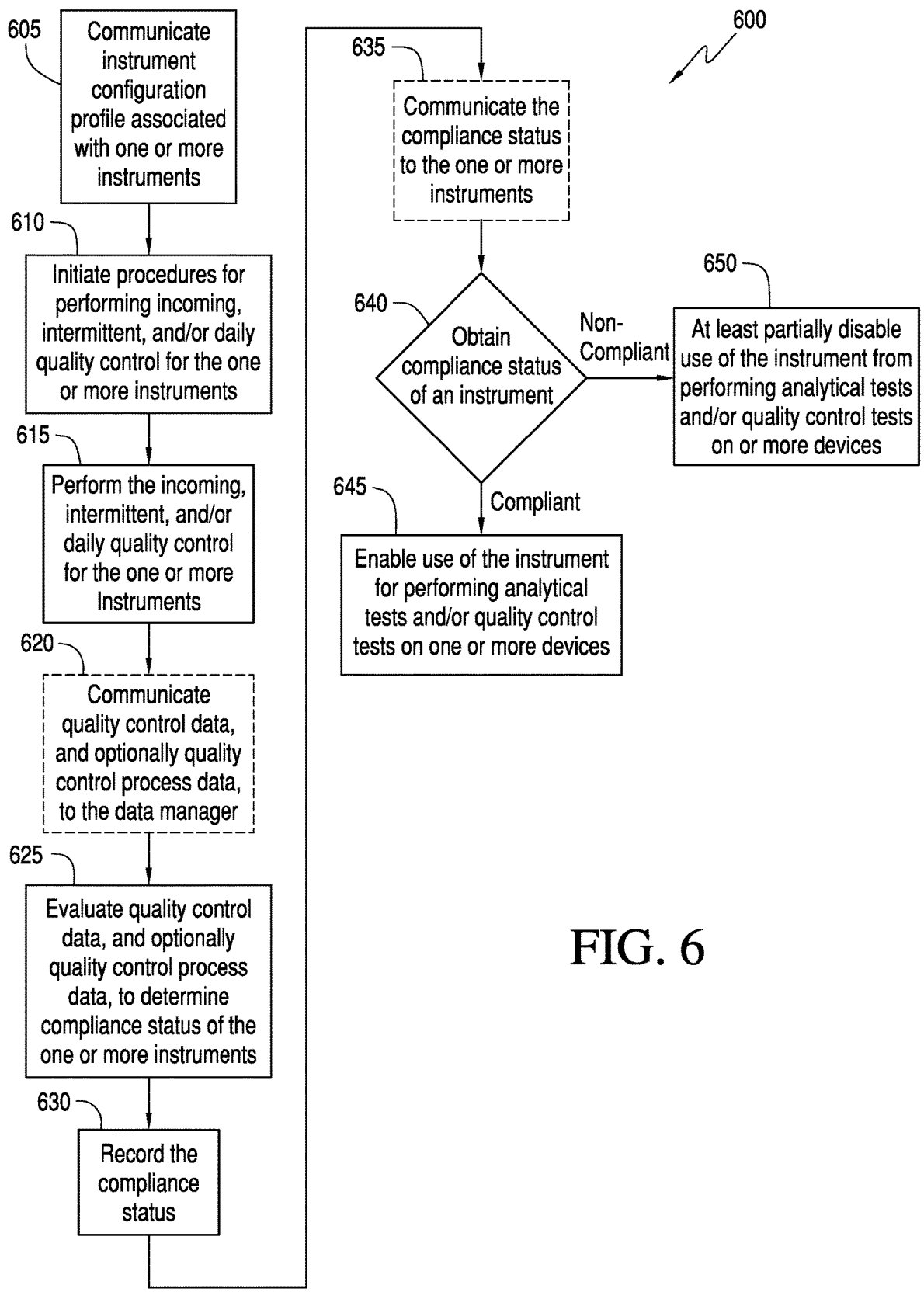

In another embodiment of the present invention, the computing devices and systems described above may be configured to perform periodic quality control for one or more instruments in accordance with one or more IQCPs. It should be understood that although the incoming, intermittent, and/or daily quality control of the instruments is supported by the present invention using the following processes, it should be understood that it may not be necessary to generate one or more IQCPs that perform such quality control based on a risk management approach. As shown in FIG. 6, a process 600 may be provided for performing incoming, intermittent, and/or daily quality control for one or more particular instruments. At step 605, an instrument configuration profile associated with the one or more instruments (e.g., instruments 305 as described with respect to FIG. 4) is communicated from a data manager (e.g., data manager 315 as described with respect to FIG. 4) to the one or more instruments to initiate the incoming, intermittent, and/or daily quality control of the one or more instruments. The instrument configuration profile includes instructions on how to perform quality control in compliance with the one or more IQCPs. For example, the instrument configuration profile may include the identification of internal and/or external quality control samples or calibrant samples to be run on devices using the one or more instruments, the thresholds or target values for the control samples or calibrant samples, the frequency of performing the quality control, and/or the identification of one or more electronic simulations to be run using the one or more instruments.

At step 610, the instrument configuration profile is configured to initiate procedures for performing the incoming, intermittent, and/or daily quality control for the one or more instruments. In preferred embodiments, the initiation procedure includes displaying a request for performance of quality control on a display of the one or more instruments in accordance with the instrument configuration profile. In additional or alternative embodiments, the initiation procedure includes providing an indicator for quality control such as a blinking light emitting diode, displaying a graphical indicator on the display of the one or more instruments, and/or sending a message to an operator of the one or more instruments (e.g., an email or text message to an external device of the operator). In any event, the procedures for performing the quality control may be triggered based on events and/or a calendar as defined within the instrument configuration profile. For example, a request for intermittent or daily quality control may be triggered upon a predetermined period of time elapsing. Alternatively, a request for intermittent quality control may be triggered upon an error message being generated by the one or more instruments. Alternatively, a request for incoming quality control may be triggered upon use of the one or more instruments for the first time in the point-of-care facility.

At step 615, the incoming, intermittent, and/or daily quality control is performed for the one or more instruments in accordance with the instrument configuration profile. In preferred embodiments, the performance of the incoming, intermittent, and/or daily quality control includes performing one or more quality control tests by running one or more quality control samples or calibration fluids defined within the instrument configuration profile on devices in order to detect one or more target analytes within the one or more quality control samples or calibration fluids. The performance of the one or more quality control tests is executed using the particular one or more instruments within the network as defined via the instrument configuration profile (e.g., the one or more instruments to which the instrument configuration profile was communicated).

In additional or alternative embodiments, the performance of the incoming, intermittent, and/or daily quality control includes performing one or more electronic simulations defined within the instrument configuration profile (i.e., controlled via the data manager) using internal program code and/or a reusable test unit that contains circuitry which provides electrical signals for testing instrument function, as discussed for example in U.S. Pat. No. 5,124,661, which is incorporated herein in its entirety. The reusable test unit mates mechanically with the connector of the instrument to test both sides of the interface with the high-impedance electrochemical domain. Circuitry within the reusable test unit produces signals for testing amperometric, conductimetric, and potentiometric measurement channels, without consuming any disposable sensor devices or requiring replenishment of chemicals. In a preferred embodiment, power to the unit is supplied through the connector from the instrument. Because the signals are produced by electrical circuitry which simulates the operation of chemical sensors, but does not employ actual sensors, no chemicals are used and no devices need be consumed for testing.

In additional or alternative embodiments, the performance of the incoming, intermittent, and/or daily quality control includes performing one or more tasks other than performing the quality control tests or one or more electronic simulations. The performance of the one or more tasks may be executed using the one or more instruments (e.g., as defined by the instrument configuration profile), the one or more terminals of the HIS or LIS, and/or the one or more external devices. For example, the one or more IQCPs may be developed to include attributes for incoming quality control that include visual inspection tasks of the one or more instruments such as visually inspecting the one more instruments for damage, functionality testing tasks such as testing connectivity functions with the network, and/or calibrating tasks such as calibrating the thermistors of the one or more instruments. Upon completions of the tasks, the results of the tasks may be evaluated and recorded using the one or more instruments, the one or more terminals of the HIS or LIS, and/or the one or more external devices.

Optionally at step 620, quality control data, and optionally quality control process data, obtained from the performance of the incoming, intermittent, and/or daily quality control is communicated to the data manager. The quality control data includes the results of the incoming, intermittent, and/or daily quality control performed using the one or more instruments, the one or more terminals of the HIS or LIS, and/or the one or more external devices such as the quality control test results, the results of the electronic simulations, and/or the results of the visual inspection of the one or more instruments. The quality control process data includes results from a variety of biologic and chemical controls and system electronic checks engineered into the instruments and/or the devices to address a number of potential errors, e.g., the determination of bubbles in a quality control sample.

At step 625, the quality control data, and optionally the quality control process data, is evaluated to determine a compliance status of one or more instruments with the plurality of attributes of the IQCP. For example, the evaluation may include comparing the quality control test results with the thresholds or target values for the control samples or calibration fluids, and optionally control rules such as Westgard Rules, comparing electronic simulation data to expected simulation data, comparing damage of the one or more instruments to acceptable damage criteria, and/or comparing temporal, process, and/or environmental conditions to a schedule or acceptable conditions. If it is determined that the quality control data, and optionally the quality control process data, comply with the attributes of the configuration profile and/or the IQCP, then the status of the one or more instruments is recorded as compliant. For example, in an instance where the quality control test results are within the thresholds or target values for the control samples or calibration fluids, or the electronic simulation data matches expected simulation data, then the status of the one or more instruments may be recorded to indicate a compliant status. However, if it is determined that the quality control data, and optionally the quality control process data, do not comply with the plurality of attributes of the IQCP, then the status of the one or more instruments is recorded as non-compliant. For example, in an instance where the quality control test results are outside the thresholds or target values for the control samples or calibration fluids, or the electronic simulation data does not match expected simulation data, then the status of one or more instruments may be recorded to indicate a non-compliant status.

In preferred embodiments, the quality control data, and optionally quality control process data, is communicated to the data manager at step 620 and the data manager evaluates the quality control data, and optionally quality control process data to determine the compliance status of the one or more instruments with the plurality of attributes of the IQCP. In alternative or additional embodiments, the one or more instruments that performed the incoming, intermittent, and/or daily quality control evaluates the quality control data, and optionally quality control process data to determine the compliance status of the one or more instruments with the plurality of attributes of the IQCP.

As should be understood, the determination of the compliance status could be, but need not be, an all or nothing evaluation where a non-compliance status is determined whenever there is non-compliance with at least one of the plurality of attributes. Instead, compliance with the attributes can be evaluated holistically by the data manager, the instrument, and/or a user, e.g., an administrator, to make a final determination on whether the one or more instruments should receive a compliant or non-compliant status. For example, in an instance where the quality control test results are within the thresholds or target values for the control samples or calibration fluids, or the electronic simulation data matches expected simulation data but the one or more of the instruments have damage such as a cracked display, then a status of the one or more of the instruments may be updated to indicate a compliant status regardless of the reported damage. Additionally, in an instance where the quality control test results are within the thresholds or target values for the control samples or calibration fluids, or the electronic simulation data matches expected simulation data but the one or more of the instruments do not have connectivity with the network, then a status of the one or more of the instruments may be updated to indicate a compliant status regardless of the connectivity issue.

Furthermore it should be understood, the determination of the compliance status could be, but need not be, a definitive compliant or non-compliant status. Instead, compliance or non-compliance with the attributes can be changed or updated by data manager, the instrument, and/or a user in view of corrective action and/or newly obtained quality control data, and optionally quality control process data. For example, in an instance where the quality control test results are outside the thresholds or target values for the control samples or calibration fluids but the quality control process data indicates that bubbles were present during the quality control test, then a status of the one or more instruments may be updated to indicate a non-compliant status. However, the data manager, the instrument, and/or a user may also be configured to implement corrective action as a result of the invalid quality control data such as requesting the quality control test(s) be repeated while taking steps to alleviate bubble formation (e.g., reduce or prevent inappropriate movement of the instrument during testing). Thereafter, if the quality control test results are now within the thresholds or target values for the control samples or calibration fluids, then a status of the one or more instruments may be updated to indicate a compliant status.

Although steps 615-625 are directed to instance in which the incoming, intermittent, and/or daily quality control is performed for the one or more instruments, it should be understood that instances in which the incoming, intermittent, and/or daily quality control is not performed are also contemplated by the present invention. For example, in instances in which the incoming, intermittent, and/or daily quality control is not performed in response to the instrument configuration profile and/or the schedule of the incoming, intermittent, and/or daily quality control, the data manager or the one or more instruments are configured to determine the compliance status of the one or more instruments as non-compliant. The determination of non-compliant may be based on the absence of the quality control data, and optionally the quality control process data, after a period of time in which it is expected that the quality control data, and optionally the quality control process data, should have been generated and/or received in response to the instrument configuration profile and/or the schedule of the incoming, intermittent, and/or daily quality control.

At step 630, the determined compliance status of the one or more instruments is recorded. In preferred embodiments, the determined compliance status of the one or more instruments is recorded or stored in a data table, e.g., a database, stored in memory of the data manager or the one or more instruments that performed the incoming, intermittent, and/or daily quality control. In additional or alternative embodiments, the data table may be stored in a data table stored in data store, e.g., data store 345 discussed with respect to FIG. 4, external to the data manager or the one or more instruments. As should be understood by those of ordinary skill in the art, the data table may be configured to include any number of instruments with corresponding identification numbers, for example a serial number or product number, and compliance statuses beyond just the one or more instruments such that the data table maintains a real time persistent record of the compliance status of all instruments within the network and available for use throughout a point-of-care facility.

Optionally at step 635, in instances in which the quality control data, and optionally quality control process data, is communicated to the data manager at step 620 and the data manager evaluates the quality control data, the compliance status of the one or more instruments is communicated back to each of the one or instruments that communicated with the data manager. The compliance status of the one or more instruments is communicated to each instrument by sending the data table as a part of the message or data packet communicated to the one or more instruments. Once the message or data packet is received by the one or more instruments, the data table with the determined compliance status is stored in memory of the one or more instruments such that each of one or more instruments are continually capable of obtaining its compliance status, and optionally the compliance status of other instruments within the network.

In instances in which the compliance status of the one or more instruments is non-compliant, the message communicated to the one or more instruments may further include corrective action that may be taken to possibly correct the failed quality control data. For example, the message may include instructions to repeat the quality control tests, take a predetermined action such as contacting a point of care coordinator in the hospital, returning the instrument to a central repository and collecting a new instrument etc. Others may include placing the instrument on a solid surface during testing, using a different set of control samples or calibration fluids, perform a power cycle of the instrument, perform calibration of the instrument, etc. Additionally, in instances in which the compliance status of the one or more instruments is non-compliant, an additional message may be communicated from the data manager or the one or more instruments to another computing system or device, e.g., an external device such as an inventory control system, a computing terminal of the administrator or laboratory personnel, and/or a computing device of maintenance personnel. The additional message may prompt or automatically trigger a request for maintenance or replacement of the one or more instruments. In accordance with aspects of the present invention, the corrective action and additional messages may be generated manually or triggered automatically in accordance with the compliance or non-compliance of the quality control data, and optionally the quality control process data, with the attributes of the configuration profile and/or the IQCP. For example, non-compliance due to quality control test results being outside the thresholds or target values for the control samples or calibration fluids may prompt or trigger calibration of the one or more instruments whereas non-compliance with a proper thermal cycling of the one or more instruments could be configured to prompt or trigger the request for maintenance or replacement of the instrument.

At step 640, each of the one or more instruments obtain their determined compliance status prior to performing an analytical test on a patient sample and/or performing another quality control test on one or more quality control samples or calibration fluids. For example, each of the one or more instruments are configured to use identification information pertaining to the instrument, for example a serial number or product number, to look up the compliance status of the instrument in the data table stored in step 630.

At step 645, when the compliance status of the instrument is compliant, the instrument is configured to operate under normal operating procedures in order to perform the analytical test and/or the another quality control test using one or more devices. For example, insertion of the one or more devices into the instrument and the confirmation of the compliant quality control compliance status executes program instructions that operate a mechanism such as a pump to apply pressure to an air-bladder forcing air through one or more conduits of one or more devices to move a metered portion of the patient sample, the quality control sample, or the calibration fluid, that is optionally amended with a compound or compounds present initially as a dry coating on an inner surface of the one or more conduits, into contact with an analyte sensor or sensors located within a detection region of the one or more conduits. Thereafter, electrical signals generated from the detection of target analyte at the analyte sensor or sensors are transmitted from the one or more devices to the instrument, where program instructions are executed to interpret the electrical signals and provide, e.g., display and/or report, a result(s) of the analytical test and/or the another quality control test.

At step 650, when the compliance status of instruments is non-compliant, the instrument is configured to be at least partially disabled from performing the analytical test and/or the another quality control test. In accordance with aspects of the present invention, the at least partial disabling of the instrument can be implemented using a number of mechanisms and does not necessarily mean that the instrument does not operate and run the analytical test and/or the another quality control test. For example, in some embodiments, the instrument may be prevented from initiating performance of the analytical test and/or the another quality control test using the one or more devices such that the analytical test and/or the another quality control test are not run using the inserted device and the inserted device is not exhausted (i.e., the instrument is completely disabled from performing the analytical test and/or the another quality control test). However, in preferred embodiments, the instrument may run the analytical test and/or the another quality control test but instead of providing the results of the analytical test and/or the another quality control test in accordance with the normal operation of the instrument, the instrument is configured to provide, e.g., display and/or report, an error message, e.g., the instrument has failed quality control (i.e., the instrument is partially disabled from performing the one or more analytical test). This mechanism would effectively prevent reporting of the results to the operator and/or the health care team.

In alternative embodiments, if the compliance status of the device is non-compliant, the instrument may be configured to run the one or more analytical tests and provide, e.g., display and/or report, the results of the one or more analytical tests. However, the display and/or reporting of the results includes a flag or some manner of indicating that the instrument has failed quality control. The flag may be configured to provide details on the failed quality control including the attributes of the IQCP that are not in compliance. In some embodiments, the details on the failed quality control may also include corrective action that may be taken to possibly correct the failed quality control.

The advantage of the aforementioned technical solution for centrally managing and implementing IQCP for quality control compliance is that it will eliminate the technical problems of having to perform a default frequency of quality control with liquid quality control or calibration fluid and an inability to balance the default frequency with instruments that include internal control systems and processes built into each instrument. For example, implementation of the steps of FIG. 6 using the computing devices and systems described above with respect to FIGS. 1-4 provide a technical contribution over conventional quality control systems and methods because the technical features of the present invention interoperate to enable or disable use of each instruments in a network based on a plurality of attributes using a centralized computing environment to ensure quality across the network of instruments and strike the right balance of liquid quality control or calibration fluid in concert with internal control processes.

Figure 7:
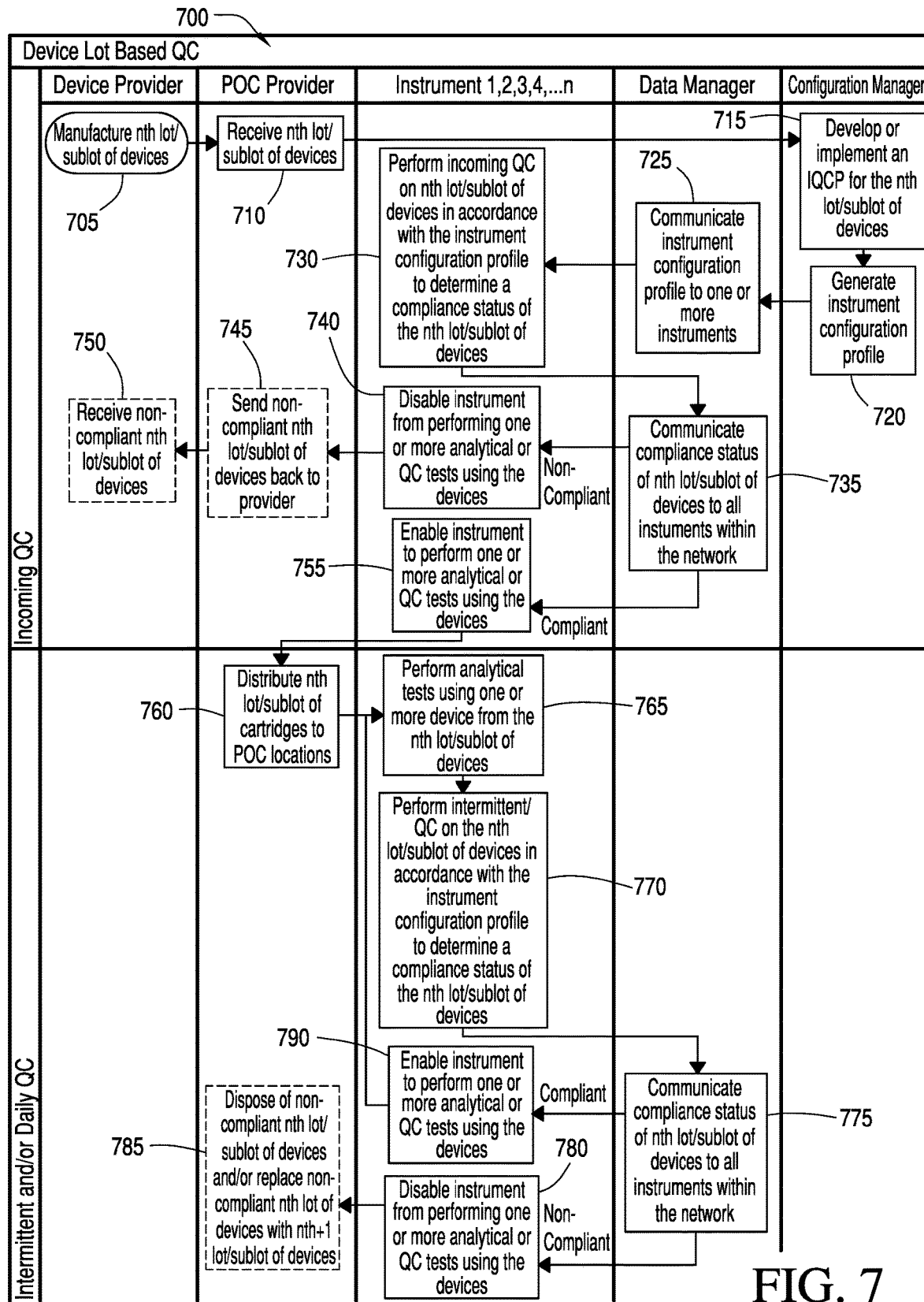

In another embodiment of the present invention, the computing devices and systems described above may be configured to develop and implement one or more IQCPs for performing incoming, intermittent, and/or daily lot based quality control for one or more devices. As shown in FIG. 7, a process 700 may be provided for developing and implementing one or more IQCPs for performing incoming, intermittent, and/or daily quality control for an nth lot/sublot of devices. At step 705, a manufacturer creates an nth lot/sublot of devices (e.g., cartridges) and ships the nth lot/sublot of devices to a customer (e.g., a point-of-care provider). The lot/sublot of devices are manufactured as identical or substantially identical products and identified using a numerical or alphanumeric lot/sublot identifier. At step 710, the a point-of-care provider receives the nth lot/sublot of devices. For example, the a point-of-care provider may scan the identification the nth lot/sublot of devices into one or more systems, e.g., the data manager, HIS, and/or LIS, and physically receive and store the nth lot/sublot of devices in an inventory such as a centrally refrigerated inventory. At step 715, the a point-of-care provider develops a new IQCP for the nth lot/sublot of devices or implements an existing IQCP for the nth lot/sublot of devices. The IQCP may be developed by laboratory personnel and/or an administrator in conjunction with a configuration manager (e.g., configuration manager 325 as described with respect to FIG. 4), or the configuration manager can be configured to automatically select a preloaded IQCP based on certain parameters such as a type of device received or the nth lot/sublot identifier of the devices received, as discussed in detail with respect to FIG. 4. The IQCP is developed to include a plurality of attributes, which are intended to ensure that a right amount and type of quality control is implemented with respect to the nth lot/sublot of devices to address the customer's specific risks and ensure quality test results.

At step 720, an instrument configuration profile associated with the nth lot/sublot of devices may be generated by the configuration manager using one or more of the plurality attributes. In preferred embodiments, the instrument configuration profile includes instructions on how to perform quality control in compliance with the IQCP including the identification of internal and/or external quality control samples to be run on the nth lot/sublot of devices, the thresholds or target values for the control samples, and the frequency of using the quality control samples. Additionally, the instrument configuration profile is designed to initiate compliance with the IQCP. At step 725, the instrument configuration profile may be communicated from the data manager to all instruments in a network, a defined instrument or subset of instruments in a network (e.g., defined via the attributes), or a randomly selected instrument or subset of instruments in a network. Thereafter, the instrument configuration profile may be configured to initiate procedures for performing incoming, intermittent, and/or daily quality control. In some embodiments, the procedure may include prompting a display of a request for performance of quality control in accordance with the instrument configuration profile on the one or more instruments in which the instrument configuration profile was communicated, on one or more terminals of the HIS or LIS, and/or on an external device associated with a user of the nth lot/sublot of devices.

At step 730, incoming quality control may be performed on the nth lot/sublot of devices in accordance with the instrument configuration profile to determine a compliance status of the nth lot/sublot of devices. The incoming quality control and determination of the compliance status is performed in a similar manner to that described with respect to steps 515-530 of FIG. 5. At step 735, the compliance status of the nth lot/sublot of devices is communicated to each instrument within the network of instruments in a similar manner to that described with respect to step 535 of FIG. 5. As should be understood, the compliance status of the nth lot/sublot of devices may be communicated to each instrument from the one or more instruments (not shown) that performed and evaluated the quality control performed on the nth lot/sublot of devices, or from the data manager (shown) which received and evaluated the results of the performance of the quality control by the one or more instruments.

At step 740, when the compliance status of the one or more of the nth lot/sublot of devices is non-compliant, the instrument is configured to be at least partially disabled from performing analytical tests and/or another quality control test in a similar manner to that described with respect to step 565 of FIG. 5. Optionally at step 745, the one or more of the nth lot/sublot of devices, which are non-compliant, may be shipped back by the point-of-care provider to the device provider as being defective. Optionally at step 750, the device provider may receive the nth lot/sublot of devices.

At step 755, when the compliance status of the one or more of the nth lot/sublot of devices is compliant, the instrument is configured to operate under normal operating procedures in order to perform analytical tests and/or other quality control tests using the one or more of the nth lot/sublot of devices in a similar manner to that described with respect to step 560 of FIG. 5. At step 760, the point-of-care provider distributes the nth lot/sublot of devices to one or more point-of-care locations, as disclosed in, for example, U.S. Pat. No. 7,552,071.

At step 765, one or more analytical test are performing using the one or more devices from the nth lot/sublot of devices in a similar manner to that described with respect to steps 540-565 of FIG. 5. At step 770, intermittent and/or daily quality control may be performed on the nth lot/sublot of devices in accordance with the instrument configuration profile to determine a compliance status of the nth lot/sublot of devices. The intermittent and/or daily quality control and determination of the compliance status is performed in a similar manner to that described with respect to steps 515-530 of FIG. 5. At step 775, the compliance status of the nth lot/sublot of devices is communicated to each instrument within the network of instruments in a similar manner to that described with respect to step 535 of FIG. 5. As should be understood, the compliance status of the nth lot/sublot of devices may be communicated to each instrument from the one or more instruments (not shown) that performed and evaluated the quality control performed on the nth lot/sublot of devices, or from the data manager (shown) which received and evaluated the results of the performance of the quality control by the one or more instruments.

At step 780, when the compliance status of the one or more of the nth lot/sublot of devices is non-compliant, the instrument is configured to be at least partially disabled from performing analytical tests and/or another quality control test in a similar manner to that described with respect to step 565 of FIG. 5. Optionally at step 785, the one or more of the nth lot/sublot of devices, which are non-compliant, may be discarded and/or replaced, as disclosed in, for example, U.S. Pat. No. 7,552,071. At step 790, when the compliance status of the one or more of the nth lot/sublot of devices is compliant, the instrument is configured to operate under normal operating procedures in order to perform analytical tests and/or other quality control tests using the one or more of the nth lot/sublot of devices in a similar manner to that described with respect to step 560 of FIG. 5.

Figure 8:
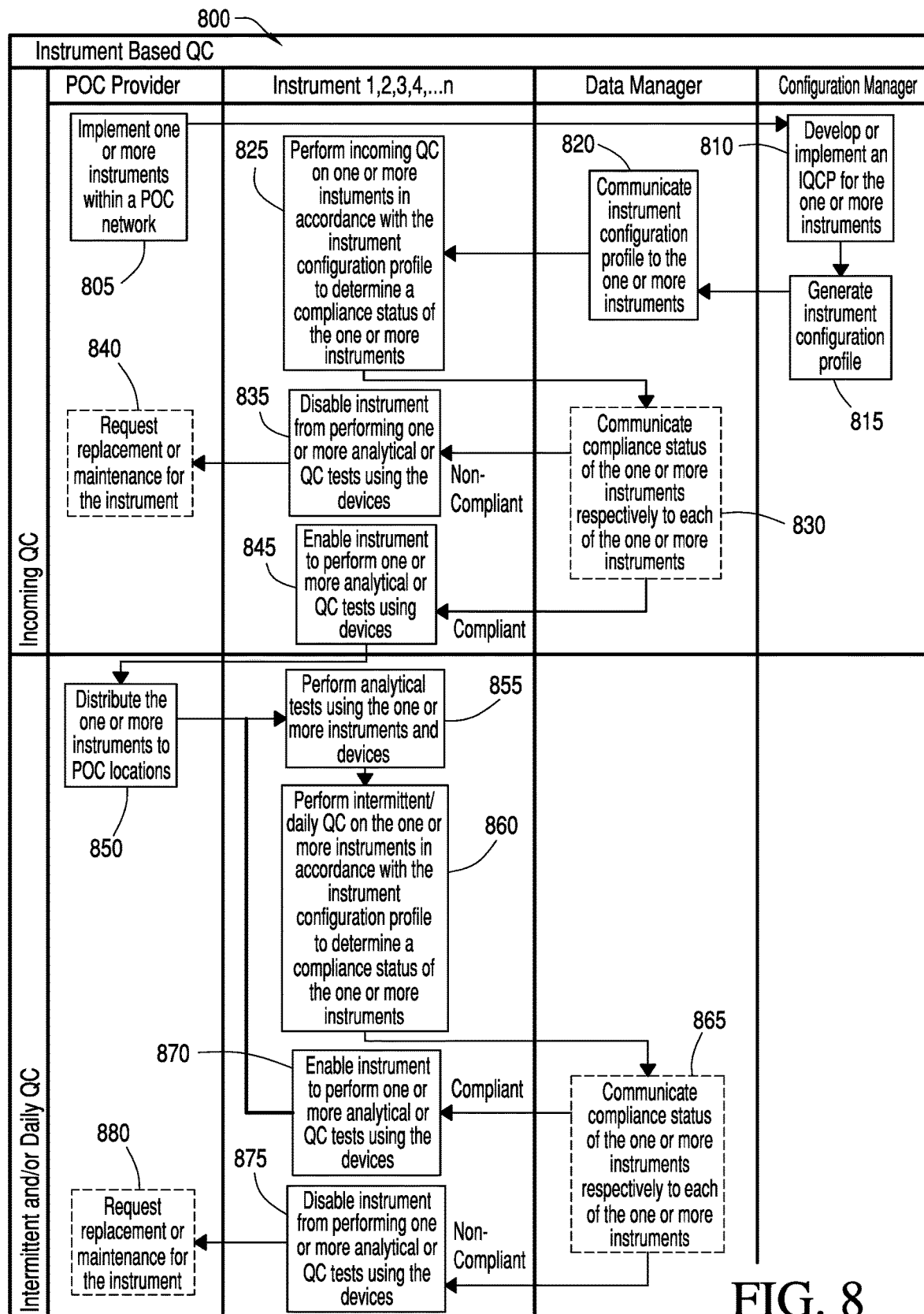

In another embodiment of the present invention, the computing devices and systems described above may be configured to develop and implement one or more IQCPs for performing incoming, intermittent, and/or daily lot based quality control for one or more instruments. As shown in FIG. 8, a process 800 may be provided for developing and implementing one or more IQCPs for performing incoming, intermittent, and/or daily quality control for one or more instrument within a point-of-care network. At step 805, a customer such as a point-of-care provider implements one or more instruments within a point-of-care network. For example, the customer may scan the identification the one or more instruments into one or more systems, e.g., the data manager, HIS, and/or LIS, and physically receive the one or more instruments in an inventory. At step 810, the customer develops a new IQCP for the one or more instruments or implements an existing IQCP for the one or more instruments. The IQCP may be developed by laboratory personnel and/or an administrator in conjunction with a configuration manager (e.g., configuration manager 325 as described with respect to FIG. 4), or the configuration manager can be configured to automatically select a preloaded IQCP based on certain parameters such as a model of instrument received or the instrument identifier of the instrument implemented, as discussed in detail with respect to FIG. 4. The IQCP is developed to include a plurality of attributes, which are intended to ensure that a right amount and type of quality control is implemented with respect to the instrument to address the customer's specific risks and ensure quality test results. It should be understood that although the incoming, intermittent, and/or daily quality control of the instruments is supported by the present invention using the following processes, it should be understood that it may not be necessary to generate one or more IQCPs that perform such quality control based on a risk management approach.

At step 815, an instrument configuration profile associated with the one or more instruments may be generated by the configuration manager using one or more of the plurality attributes. In preferred embodiments, the instrument configuration profile includes instructions on how to perform quality control in compliance with the IQCP including the identification of internal and/or external quality control samples or calibration fluids to be run on the one or more instruments, the thresholds or target values for the control samples or calibration fluids, and the frequency of using the quality control samples or calibration fluids. Additionally, the instrument configuration profile is designed to initiate compliance with the IQCP. At step 820, the instrument configuration profile may be communicated from the data manager to all instruments in a network, a defined instrument or subset of instruments in a network (e.g., defined via the attributes), or a randomly selected instrument or subset of instruments in a network. Thereafter, the instrument configuration profile may be configured to initiate procedures for performing the incoming, intermittent, and/or daily quality control. In some embodiments, the procedure may include prompting a display of a request for performance of quality control in accordance with the instrument configuration profile on the one or more instruments in which the instrument configuration profile was communicated, on one or more terminals of the HIS or LIS, and/or on an external device associated with a user of the one or more instruments.

At step 825, incoming quality control may be performed on the one or more instruments in accordance with the instrument configuration profile to determine a compliance status of one or more instruments. The incoming quality control and determination of the compliance status is performed in a similar manner to that described with respect to steps 615-630 of FIG. 6. Optionally at step 830, in instances in which the quality control data, and optionally quality control process data, is communicated to the data manager at step 825 and the data manager evaluates the quality control data, the compliance status of the one or more instruments is communicated back respectively to each of the one or instruments in a similar manner to that described with respect to step 635 of FIG. 6.

At step 835, when the compliance status of one or more instruments is non-compliant, the one or more instruments are configured to be at least partially disabled from performing analytical tests and/or another quality control test in a similar manner to that described with respect to step 650 of FIG. 6. Optionally at step 840, a request may be issued for replacement or maintenance of the non-compliant one or more instruments in a similar manner to that described with respect to step 635 of FIG. 6.

At step 845, when the compliance status of the one or more instruments is compliant, the one or more instruments are configured to operate under normal operating procedures in order to perform analytical tests and/or other quality control tests using one or more devices in a similar manner to that described with respect to step 645 of FIG. 6. At step 850, the point-of-care provider distributes the one or more instruments to one or more point-of-care locations.

At step 855, one or more analytical test are performing using the one or more instruments in a similar manner to that described with respect to step 645 of FIG. 6. At step 860, intermittent and/or daily quality control may be performed on the one or more instruments in accordance with the instrument configuration profile to determine a compliance status of the one or more instruments. The intermittent and/or daily quality control and determination of the compliance status is performed in a similar manner to that described with respect to steps 615-630 of FIG. 6. Optionally at step 865, in instances in which the quality control data, and optionally quality control process data, is communicated to the data manager at step 855 and the data manager evaluates the quality control data, the compliance status of the one or more instruments is communicated back respectively to each of the one or instruments in a similar manner to that described with respect to step 635 of FIG. 6.

At step 870, when the compliance status of the one or more instruments is compliant, the one or more instruments are configured to operate under normal operating procedures in order to perform analytical tests and/or other quality control tests using one or more devices in a similar manner to that described with respect to step 645 of FIG. 6. At step 875, when the compliance status of one or more instruments is non-compliant, the one or more instruments are configured to be at least partially disabled from performing analytical tests and/or another quality control test in a similar manner to that described with respect to step 650 of FIG. 6. Optionally at step 880, a request may be issued for replacement or maintenance of the non-compliant one or more instruments in a similar manner to that described with respect to step 635 of FIG. 6.

While the invention has been described in terms of various preferred embodiments, those skilled in the art will recognize that various modifications, substitutions, omissions and changes can be made without departing from the spirit of the present invention. It is intended that the scope of the present invention be limited solely by the scope of the following claims. In addition, it should be appreciated by those skilled in the art that a plurality of the various embodiments of the invention, as described above, may be coupled with one another and incorporated into a single reader device.

We claim:

1. A portable clinical analyzer for in vitro analysis, the analyzer comprising:
   a port configured to receive a sample testing cartridge of a set of sample testing cartridges; and
   a computing device configured to:
   receive an instrument configuration profile associated with the portable clinical analyzer;
   in response to receiving the instrument configuration profile, prompt a user to initiate procedures for performance of analyzer calibration verification in accordance with the instrument configuration profile, wherein the instrument configuration profile includes: (i) identification of a predetermined number and type of calibration fluids and a predetermined number of sample testing cartridges of the set of sample testing cartridges to be used for the performance of the analyzer calibration verification, or (ii) identification of an electronic simulation to be used for the performance of the analyzer calibration verification;
   control the portable clinical analyzer to perform the analyzer calibration verification using: (i) the predetermined number and type of calibration fluids and & the predetermined number of sample testing cartridges of the set of sample testing cartridges, or (ii) the electronic simulation, to generate calibration verification data;
   transmit the calibration verification data to a data manager;
   receive a message from the data manager, wherein the message includes a data table comprising: (i) an identification number associated with each analyzer within a group of analyzers including the portable clinical analyzer, and (ii) a compliance status for each analyzer within the group of analyzers including the portable clinical analyzer, wherein the compliance status is a binary determination of either compliant or non-compliant for each analyzer within the group of analyzers;

storing the data table in memory of the portable clinical analyzer such that the portable clinical analyzer is continually capable of obtaining the compliance status for the portable clinical analyzer and other analyzers within the group of analyzers;

obtaining the compliance status for the portable clinical analyzer from the data table stored in the memory of the portable clinical analyzer based on an identification number associated with the portable clinical analyzer;

when the compliance status obtained from the data table indicates the portable clinical analyzer is in compliance, enable use of the portable clinical analyzer for performing one or more analytical tests on biological samples; and when the compliance status obtained from the data table indicates the portable clinical analyzer is not in compliance, at least partially disable use of the portable clinical analyzer for performing the one or more analytical tests on the biological samples.

2. A system comprising:

a set of sample testing cartridges;

a plurality of analyzers in communication with one another via a wireless network, wherein each analyzer of the plurality of analyzers comprises a processor configured to:

receive an instrument configuration profile;

in response to receiving the instrument configuration profile, prompt a user to initiate procedures for performance of analyzer calibration verification in accordance with the instrument configuration profile, wherein the instrument configuration profile includes: (i) identification of a predetermined number and type of calibration fluids and a predetermined number of sample testing cartridges of the set of sample testing cartridges to be used for the performance of the analyzer calibration verification, or (ii) identification of an electronic simulation to be used for the performance of the analyzer calibration verification;

control the analyzer to perform the analyzer calibration verification using: (i) the predetermined number and type of calibration fluids and the predetermined number of sample testing cartridges of the set of sample testing cartridges, or (ii) the electronic simulation, to generate calibration verification data; and transmit the calibration verification data;

a data manager that is in communication with each analyzer of the plurality of analyzers via the wireless network, wherein the data manager is configured to:

communicate the instrument configuration profile to the plurality of analyzers;

receive a first set of the calibration verification data from a first analyzer of the plurality of analyzers;

receive a second set of the calibration verification data from a second analyzer of the plurality of analyzers;

determine a first compliance status of the first analyzer based on whether the first set of the calibration verification data is within range of predetermined calibration target values, wherein the first compliance status is a binary determination of either compliant or non-compliant;

determine a second compliance status of the second analyzer based on whether the second set of the calibration verification data is within range of the predetermined calibration target values, wherein the second compliance status is a binary determination of either compliant or non-compliant;

store the determined first compliance status of the first analyzer as either compliant or non-compliant and the second compliance status of the second analyzer as either compliant or non-compliant in a data table;

communicate a first message to the first analyzer, wherein the first message includes the data table, and wherein when the first compliance status indicates the first analyzer is non-compliant, the first message further includes corrective action to be taken to correct the first set of the calibration verification data; and communicate a second message to the second analyzer, wherein the second message includes the data table, and wherein when the second compliance status indicates the second analyzer is non-compliant, the second message further includes corrective action to be taken to correct the second set of the calibration verification data, wherein a first processor of the first analyzer is configured to:

receive the first message with at least the data table and store the data table in memory of the first analyzer;

obtain the first compliance status for the first analyzer from the data table stored in the memory of the first analyzer;

when the first compliance status obtained from the data table indicates the first analyzer is compliant, enable use of the first analyzer for performing one or more analytical tests on biological samples; and when the first compliance status obtained from the data table indicates the first analyzer is non-compliant, at least partially disable use of the first analyzer for performing the one or more analytical tests on the biological samples and provide the corrective action to be taken to correct the first set of calibration verification data; and wherein a second processor of the second analyzer is configured to:

receive the second message with at least the data table and store the data table in memory of the second analyzer;

obtain the second compliance status for the second analyzer from the data table stored in the memory of the second analyzer;

when the second compliance status obtained from the data table indicates the second analyzer is compliant, enable use of the second analyzer for performing the one or more analytical tests on biological samples; and when the second compliance status obtained from the data table indicates the second analyzer is non-compliant, at least partially disable use of the second analyzer for performing the one or more analytical tests on the biological samples and provide the corrective action to be taken to correct the second set of calibration verification data.

3. The system of claim 2, further comprising a configuration manager configured to obtain the predetermined calibration target values, and transmit the instrument configuration profile with the predetermined calibration target values to the data manager.

4. The system of claim 2, wherein the one or more analytical tests are configured to detect one or more analytes selected from the group consisting of: sodium, potassium, chloride, total carbon dioxide, ionized calcium, glucose, blood urea nitrogen (BUN), creatinine, lactate, hematocrit, pH, partial pressure of carbon dioxide, partial pressure of oxygen, troponin I, troponin T, creatine kinase MB, procalcitonin, beta human chorionic gonadotropin (bHCG), human chorionic gonadotropin (HCG), N-terminal of the prohormone brain natriuretic peptide (NTproBNP), prohormone brain natriuretic peptide (proBNP), brain natriuretic peptide (BNP), myoglobin, parathyroid hormone, d-dimer, neutrophil gelatinase-associated lipocalin (NGAL), galectin-3, and prostate specific antigen (PSA).

5. The system of claim 2, wherein the predetermined number of calibration fluids is one to five.

6. The system of claim 2, wherein the predetermined number of the sample testing cartridges of the set of sample testing cartridges is one to five.

7. The system of claim 2, wherein the data manager is further configured to:
generate a schedule comprising a scheduled time for the analyzer calibration verification for each analyzer of the plurality of analyzers; and
transmit the instrument configuration profile to each analyzer of the plurality of analyzers in accordance with the schedule.

8. The system of claim 7, wherein the data manager is further configured to reset a scheduled time for the analyzer calibration verification for each analyzer of the plurality of analyzers that has a determined compliance status that indicates compliance.

9. The system of claim 2, wherein the data manager is further configured to send a request for a replacement analyzer for each analyzer of the plurality of analyzers that has a determined compliance status that indicates not in compliance.

10. The system of claim 2, wherein the data manager is further configured to send a request for maintenance for each analyzer of the plurality of analyzers that has a determined compliance status that indicates not in compliance.

11. The system of claim 2, wherein the prompting the user to initiate the procedures for the performance of the analyzer calibration verification includes displaying a request for the performance of the analyzer calibration verification on a display of an analyzer in accordance with the instrument configuration profile.

12. The system of claim 2, wherein the identified electronic simulation is performed by an electronic simulator configured to use mathematical models to replicate behavior of a sample testing cartridge in communication with an analyzer.

13. The system of claim 12, wherein each analyzer of the plurality of analyzers further comprises the electronic simulator.

14. The system of claim 12, wherein the electronic simulator is a separate computing device from the processor of each analyzer of the plurality of analyzers.

15. A computer implemented method comprising:
receiving, at an analyzer, an instrument configuration profile associated with the analyzer, wherein the analyzer is part of a group of analyzers in communication with one another via a wireless network;
in response to receiving the instrument configuration profile, prompting, by the analyzer, a user to initiate procedures for performance of analyzer calibration verification in accordance with the instrument configuration profile, wherein the instrument configuration profile includes:
identification of a predetermined number and type of calibration fluids and a predetermined number of sample testing cartridges of a set of sample testing cartridges to be used for the performance of the analyzer calibration verification;
performing, by the analyzer, one or more quality control tests to generate calibration verification data, the one or more quality control tests being performed using: (i) the predetermined number and type of calibration fluids, and (ii) the predetermined number of sample testing cartridges of the set of sample testing cartridges;
transmitting, by the analyzer, the calibration verification data to a data manager;
receiving, at the analyzer, a message from the data manager, wherein the message includes a data table comprising: (i) an identification number associated with each analyzer within the group of analyzers including the analyzer, and (ii) a compliance status for each analyzer within the group of analyzers including the analyzer, wherein the compliance status is a binary determination of either compliant or non-compliant for each analyzer within the group of analyzers;
storing, at the analyzer, the data table in memory of the analyzer such that the analyzer is continually capable of obtaining the compliance status for the analyzer and other analyzers within the group of analyzers;
obtaining, by the analyzer, the compliance status for the analyzer from the data table stored in the memory of the analyzer based on an identification number associated with the analyzer;
when the compliance status obtained from the data table indicates the analyzer is in compliance, enable use of the analyzer for performing one or more analytical tests on biological samples; and
when the compliance status obtained from the data table indicates the analyzer is not in compliance, at least partially disable use of the analyzer for performing the one or more analytical tests on the biological samples.

* * * * *